United States Patent [19]
Macfarlane et al.

[11] Patent Number: 6,128,516
[45] Date of Patent: *Oct. 3, 2000

[54] METHOD AND APPARATUS FOR DETECTING AND MEASURING CONDITIONS AFFECTING COLOR

[75] Inventors: Darby Simpson Macfarlane; David Kenneth Macfarlane, both of Hastings-on-Hudson; Fred W. Billmeyer, Jr., Schenectady, all of N.Y.

[73] Assignee: Chromatics Color Sciences International Inc., New York, N.Y.

[ * ] Notice: This patent is subject to a terminal disclaimer.

[21] Appl. No.: 08/939,583

[22] Filed: Sep. 29, 1997

Related U.S. Application Data

[62] Division of application No. 08/239,733, May 9, 1994, Pat. No. 5,671,735.

[51] Int. Cl.$^7$ .......................................... A61B 5/00
[52] U.S. Cl. ..................... 600/310; 600/315; 600/476; 356/405
[58] Field of Search ..................... 600/310, 315, 600/322, 473, 476, 477; 356/402, 405, 421

[56] References Cited

U.S. PATENT DOCUMENTS

| Re. 31,815 | 1/1985 | Alfano . |
| 205,578 | 7/1878 | Rose et al. . |

(List continued on next page.)

FOREIGN PATENT DOCUMENTS

| 655221 | 5/1995 | European Pat. Off. . |
| 1347400 | 11/1963 | France . |
| 1468339 | 12/1966 | France . |
| 2587181 | 3/1987 | France . |
| 1236984 | 3/1967 | Germany . |
| 3827457 | 6/1989 | Germany . |
| 57-28338 | of 1982 | Japan . |
| 59-020824 | 2/1984 | Japan . |
| 0037896 | 8/1985 | Japan . |
| 0257328 | 12/1985 | Japan . |
| 8401665 | 12/1985 | Netherlands . |
| 2001595 | 10/1993 | Russian Federation . |

OTHER PUBLICATIONS

Gibson, "Measurement of skin color in vivo," Journal of the Society of Cosmetic Chemists, vol. 22, pp. 725–740, Oct. 1971.

Measurement of skin colour in vivo, Gibson Journal of the Society of Cosmetic Chemists, vol. 22, pp. 725–740 (1971).

(List continued on next page.)

*Primary Examiner*—Eric F. Winakur
*Attorney, Agent, or Firm*—Baker Botts L.L.P.

[57] ABSTRACT

A method and apparatus for determining the condition of a test subject based on color uses a color measuring instrument to detect change in a color factor indicative of a condition such as a disease, spoilage, ageing, etc. A medical condition such as bilirubinemia that affects skin color can be detected. One measures color factors such as Hunter b and L in the subjects' skin color. For predetermined ranges of one color factor, in particular L, changes in the other color factor, e.g. Hunter b, above predetermined levels are indicative of the medical condition. In many cases, a single measurement of the color factors can be utilized as a warning of the likelihood of the medical or contaminated condition, if the ordinary range of the color factor is known for healthy individuals with skin coloration like that of the test subject. Even if there has been no baseline measurement and the test subject's color is such that a single reading of one or two color factors will not warn of the possible presence of the medical condition or contamination, sequential readings can indicate the presence or absence of the condition based upon changes in the measured color factor, or lack of changes. The color measuring techniques apply to a wide range of biological test subjects (e.g. hair, teeth, tissue, excretions, foods, soil, animals, plants).

174 Claims, 3 Drawing Sheets

U.S. PATENT DOCUMENTS

| | | |
|---|---|---|
| 1,582,122 | 4/1926 | Clapp . |
| 1,629,330 | 5/1927 | Adler . |
| 1,741,080 | 12/1929 | Stenz . |
| 1,979,119 | 10/1934 | Radzinsky . |
| 2,221,774 | 11/1940 | Bowser . |
| 3,003,388 | 10/1961 | Hunter et al. . |
| 3,533,399 | 10/1970 | Goldberg et al. . |
| 3,736,064 | 5/1973 | Kent et al. . |
| 4,029,085 | 6/1977 | Dewitt et al. . |
| 4,093,991 | 6/1978 | Christie, Jr. et al. . |
| 4,135,497 | 1/1979 | Meyers et al. . |
| 4,241,738 | 12/1980 | Lübbers et al. . |
| 4,267,844 | 5/1981 | Yamanishi . |
| 4,302,971 | 12/1981 | Luk . |
| 4,357,106 | 11/1982 | Tschirren et al. . |
| 4,423,736 | 1/1984 | Dewitt et al. . |
| 4,434,467 | 2/1984 | Scott . |
| 4,479,499 | 10/1984 | Alfano et al. . |
| 4,561,850 | 12/1985 | Fabbri et al. . |
| 4,654,794 | 3/1987 | O'Brien . |
| 4,681,546 | 7/1987 | Hart . |
| 4,723,554 | 2/1988 | Oman et al. . |
| 4,813,000 | 3/1989 | Wyman et al. . |
| 4,842,523 | 6/1989 | Bourdier et al. . |
| 4,857,071 | 8/1989 | Anderson . |
| 4,877,034 | 10/1989 | Atkins et al. . |
| 4,894,547 | 1/1990 | Leffell et al. . |
| 4,909,632 | 3/1990 | Macfarlane . |
| 4,964,874 | 10/1990 | Saphakkul . |
| 5,127,406 | 7/1992 | Yamaguchi . |
| 5,161,553 | 11/1992 | Cohen et al. . |
| 5,259,382 | 11/1993 | Kronberg . |
| 5,311,293 | 5/1994 | Macfarlane et al. . |
| 5,313,267 | 5/1994 | Macfarlane et al. . |
| 5,337,745 | 8/1994 | Benaron et al. . |
| 5,344,463 | 9/1994 | Chan et al. . |
| 5,353,790 | 10/1994 | Jacques et al. . |
| 5,387,977 | 2/1995 | Berg et al. . |
| 5,424,545 | 6/1995 | Block et al. ............................ 356/405 |
| 5,671,735 | 9/1997 | Macfarlane et al. ................... 356/405 |

OTHER PUBLICATIONS

Abstract, A New Computer–Driven Skin Bilirubinometer: Preliminary Evaluation, Tayaba et al., Pediatric Research, Apr. 1993, 33 A239.

C. Jackson, *Color Me Beautiful,* New York, Ballantine Books, Apr. 1981, pp. 25, 26, Color Palettes, 37–39, 41–59, 61–74, 143–147.

G. Pickney et al., *Your New Image Through Color & Line,* California Fashion Image/Crown Summit Books, Sep. 1981, pp. 1–3, 17, 21–29, 97–105, 111, 112, 120–127.

R. Evans, *An Introduction To Color,* Wiley, New York, 1948, pp. 26–27 and 87–90.

C.S. McCamy et al., A Color–Rendition Chart, J. Appl. Photogr. Eng. vol. 2, pp. 95–99 (1976).

C.A. Pearson, Face Colour As A Sign of Tuberculosis, Color Res. Apprl. Vol. 7, pp. 31–33, (1982).

P.A. Lovett et al., Measurement of the Skin Color of Babies in Hospital, Proc. of CIBS Lighting Conference, 1986, HMSO, London, 1986, pp. 140–154.

G. Wyszecki et al., *Color Science,* 2nd Edition (1982) Table of Contents, p. 63–72.

Advertisement for digital photometer by Photo Research in *Optical Spectra,* Nov., 1973.

Advertisement for light meters sold by Minolta Corporation in *Studio Photography,* Nov. 1981, vol. 17, No. 11.

F. Billmeyer & M. Saltzman, "Principles of Color Technology," 2nd ed., John Wiley & Sons, New York, NY 1981 pp. 18–19, 59–61, 92.

M. Kenny et al. "Transcutaneous Bilirubin Monitoring of Newborns", *Annals of the New York Academy of Sciences,* vol. 428, pp. 251–262 (1984).

R.E. Hannemann et al., "Neonatal Serum Bilirubin from Skin Reflectance", *Pediatric Research,* vol. 12, pp. 207–210 (1978).

F. Billmeyer, Jr., "Quantifying Color Apperance Visually and Instrumentally", *Color Research and Application,* vol. 13, pp. 140–145 (1988).

T. Hegyi, M.D., "Transcutaneous Bilirubinometry In The Newborn Infant: State of the Art", *Journal of Clinical Monitoring,* vol. 2, pp. 53–59 (1986).

R.E. Hanneman et al., "Evaluation of Minolta Bilirubin Meter as a Screening Device", *Pediatrics,* vol. 69, pp. 107–109 (1982).

D. Onks et al., "Effect of Melanin, Oxyhemoglobin and Bilirubin on Transcutaneous Bilirubinometry", *Acta. Peadiatrica,* vol. 82, pp. 19–21 (1993).

F.D. Ortega et al., "Bilirrubinometria Transcutanea: Correlacion del Area de Medida Con La Espectropometria y Colorimetria Por Diazorreaccion", Am. Exp. Pediarr., vol. 39, pp. 438–440 (1993).

R.E. Schumacher, "Noninvasive Measurement of Bilirubin in the Newborn", *Clinics in Perinatology,* vol. 17, pp. 417–435 (1990).

I. Yamanouchi et al., "Transcutaneous Bilirubinometry: Preliminary Studies of Noninvasive Transcutaneous Bilirubin Meters in the Okayama National Hospital", *Pediatrics,* vol. 65, pp. 195–202 (1980).

Advertisement for portable photometer by Photo Research in *Optica Spectra,* Nov., 1973.

D. Tudehope et al., "Non–invasive method of measuring bilirubin levels in newborn infants", *The Medical Journal of Australia,* vol. 1, pp. 165–168 (1982).

W.A. Gerrard et al., The Measurement of Hair Colour, International Journal of Cosmetic Science, vol. 11, pp. 97–101 (1989).

METHOD AND APPARATUS FOR DETECTING AND MEASURING CONDITIONS AFFECTING COLOR

This is a division of U.S. patent application Ser. No. 08/239,733 filed on May 9, 1994, now patent No. 5,671,735. No right of priority is claimed based upon any application filed earlier than May 9, 1994.

BACKGROUND OF THE INVENTION

This invention relates to a method and apparatus for the detection and/or measurement of a condition that affects the color of a biological test subject, and more particularly to a process and instrument for measuring at least one color characteristic or factor of the biological test subject indicative of the condition of interest.

Visual observation of a subject for changes in coloration indicative of a particular condition has often occurred. The subject may be a person or animal being observed to determine the presence or absence of a medical condition. The color characteristics or a single color characteristic of other test subjects such as biopsy specimens or excretions have diagnostic value.

An individual person's skin color is often assessed by her or his doctor. Hypertension, tuberculosis, sclerosis of the liver, to name just a few, are examples of ailments with symptomatic skin color changes among at least a sizeable population segment. Hair color evaluation and dental coloration evaluation are valuable. These may bear on the health of the individual, the health of the individual's hair and teeth, or these may permit accurate cosmetic activities, for example, to counteract graying or to accurately match new dental work to existing teeth.

Likewise, the condition of plants and agricultural products IS visually inspected for color as an indication of condition. Contamination of soil is likewise apparent from visual inspection. Such visual inspections are subjective. Measuring by instrument color characteristics that are key to the visual inspection has the benefit of objectivity and consistency.

In the past, hyperbilirubinemia in newborns has been detected by visually observing an individual for jaundice or by routinely taking and testing a blood sample. Upon detection, hyperbilirubinemia has been treated by phototherapy. During the course of phototherapy, blood samples have been taken and tested at regular intervals until it was determined that the level of serum bilirubin had decreased to an acceptable level.

In infants, there is little blood available for use in the blood testing for hyperbilirubinemia. So much blood is drawn that transfusions are often necessary to replace the drawn blood. The newborn is thereby exposed to all of the risks that transfusions bring. Blood sampling and transfusions are, of course, painful to the newborn, and as with any invasive procedure, both present medical risks, such as for example, risk of infection. There is a need, therefore, for a reliable, noninvasive technique for detecting and measuring a skin color affecting medical condition such as hyperbilirubinemia.

This is one example of a wider need for procedures and instruments to objectively and consistently determine a color characteristic or factor indicative of the condition of a test subject or indicative of a particular ailment or condition. The methods and apparatus of this invention can be employed where previously visual inspection of which example are given above, have been carried out at least in part on observable color characteristics.

BRIEF SUMMARY OF THE INVENTION

According to this invention there is provided a method and apparatus for detecting and quantitatively measuring a condition affecting the color of a test subject. The method includes measuring at least one color characteristic of the subject.

In one exemplary procedure according to this invention at least one color characteristic is measured at least at first and second points in time and compared for change to test for hyperbilirubinemia. In the preferred procedure a second skin color characteristic is also measured on the basis of which the subject can be assigned to one of plural categories among which varying amounts of change in the first-mentioned skin color characteristic are indicative of the presence of the medical condition. The first characteristic is then observed for a change of measured value sufficient to indicate the medical condition for a subject in that category. Preferably, a base reading of at least the first color characteristic is first made at a time the subject is without characteristic skin color change indicative of the medical condition for which he or she is to be tested.

In the case of hyperbilirubinemia detection, the first skin color characteristic is Hunter b, which is a color factor dependent on the relative content, in a color, of two opponent colors, yellow and blue. Hunter b is a factor comprising a first function (Y) weighted in a first portion of the spectrum, the yellower portion, a second function (Z) weighted in a second portion of the spectrum, the bluer portion, and a weighting term ($1/Y^{1/2}$) that is a function of the lightness of a color and that decreases the value of the color factor as lightness increases. Y and Z are part of the three tristimulus values X, Y and Z known to the color scientist for the purpose of defining a color. They are measurable by commercially available instruments such a colorimeters.

In the case of testing newborns for hyperbilirubinemia, readings of Hunter b and the Hunter lightness measure L are made shortly after birth. These can provide the base reading since hyperbilirubinemia does not manifest itself immediately after birth. The first reading is made typically within preferably five hours, but as soon as possible after birth. Subsequent readings, beginning are then made during the next few days. The subsequent readings of Hunter b are compared with the first, baseline reading of Hunter b to determine whether Hunter b has increased to an extent that indicates a degree of jaundice characteristic of hyperbilirubinemia for a person having the subject's particular skin lightness L. L is measured during each subsequent test to be sure that it remains close to the original reading. This gives a degree of confidence that the test procedures are being conducted appropriately.

In the event that the medical condition affecting skin color is detected in a procedure like that described above for hyperbilirubinemia, then the measuring of skin color characteristics continues at regular intervals until the symptomatic color characteristic abates sufficiently to indicate the individual's recovery from the medical condition. In the case of hyperbilirubinemia, phototherapy is administered once a sufficient change in Hunter b is observed to indicate the jaundice of hyperbilirubinemia. Throughout the course of phototherapy, then, the Hunter b and L characteristics are continually monitored until the jaundice has been eliminated. This is valuable in removing the newborn from under the phototherapy lamps, since there is the danger of damage to the newborn's eyes in the event eye protection is prematurely removed or accidentally dislodged.

The apparatus used in accordance with this invention includes a color measuring device such as a colorimeter and computational means for storing and comparing the characteristic or characteristics that are measured when testing for the medical condition. Where Hunter b is measured for the purpose of detecting hyperbilirubinemia, a colorimeter capable of calculating Hunter b and L can be used. This can be a commercially available colorimeter with this capability. The computational means preferably has sufficient memory to store one or more previous readings and should be programmed to compare previous and current readings to detect changes in Hunter b and L. Preferably the colorimeter and the computational means are integrated in a single instrument, but the commercial colorimeter can be utilized in cooperation with, for example, a personal computer, which stores and can compare Hunter b and L values from measurements taken at timed intervals. Likewise, the computational means, whether an integrated part of the instrument or a separate computer, can be used to store ranges of lightness L and the increase in Hunter b that, for the various lightness ranges, indicate an unacceptable increase in serum bilirubin.

Preferably, each skin color characteristic measurement used to assess the presence or absence of the condition for which testing is carried out is actually an average of multiple tests. For example, when newborns are tested for the jaundice that signals hyperbilirubinemia, multiple readings are made at multiple sites. Five or six of the readings from which Hunter b and L (and perhaps a third characteristic, Hunter a, as described below) are made at, for example, each of several locations which may include some or all of two forehead locations, at least one chest location, a cheek location and two back locations. At each site, the Hunter readings that have the highest and lowest values of b are discarded, then all of the readings of each Hunter characteristic are averaged. Subsequent readings are made in the same manner and compared. As used herein, "Hunter a, b and L" includes such average values, but is not limited to just the values arrived at by the averaging technique unless expressly so-limited. The discarding and averaging is readily accomplished by the computational provisions of the test equipment. The averaging technique may improve the testing of other than skin color where the testing steps of this invention are used, for example in the evaluation of hair by color measurement.

In skin color testing, it is important to cleanse the site utilizing a cleansing agent that does not contribute any coloration. Likewise, when testing is carried out on test subjects other than an individual's skin, the test subject should be free of any color altering contaminant. In skin color testing, the site on the test subject should be dry, and in all cases the instrument should have the capability of being applied to the site in such a manner that ambient light does not enter the instrument.

When testing in the manner described above, it is preferred to test for a third characteristic, as well, and using historical experience, determine whether that third characteristic lies outside an expected range of values, taking into account the values measured for the first and second characteristics. When testing for hyperbilirubinemia in the above procedure, the third characteristic is Hunter a. If the third characteristic is observed to have a value outside the range of normal expectations this may be an indication of error in the test procedure, in which case one conducting the test would not want to rely on the test results.

Determination of the first and second skin color characteristics at just one point in time can indicate or strongly suggest a medical condition affecting skin color if the first characteristic measurement is observed to lie outside a range of values for that characteristic known by experience to be normal for a subject having the particular measured value of the second characteristic. For example, in many individuals hyperbilirubinemia is strongly suggested if Hunter b and L are measured and it is determined that, based on skin color categories previously observed, Hunter b is above any ordinary value for a subject with skin having the L value measured. Also, even if baseline readings of Hunter b and L (and preferably a) are not made, changes in the value of Hunter b can signal the presence of hyperbilirubinemia if measurements of the Hunter values are made at timed intervals in the foregoing fashion. Out of the ordinary increases in Hunter b, for example, two or more points, can be an indication of hyperbilirubinemia when the measured L value remains in a constant range from one measurement to the next. Similarly, large decreases in Hunter b, of for example two or more, can be an indication of hyperbilirubinemia from which the infant is recovering, again if L remains relatively constant.

Significant testing has established the value of the foregoing techniques in detecting hyperbilirubinemia. The same techniques will indicate other jaundice-producing medical conditions in human and animal subjects. Hepatitis or liver disorders are examples of such medical conditions susceptible to diagnosis with the methods and apparatus of this invention.

Tuberculosis has been observed to affect skin color in dark skinned individuals such as many persons of African descent. Appropriate color measurement in accordance with this invention may provide a valuable diagnostic tool.

Biopsy specimens, body fluids, excretions, etc. are visually inspected for color. The techniques and instrumentation according to this invention can provide objectivity and consistency to such inspections.

The above and further advantages of this invention will be better understood with reference to the following detailed description of the preferred embodiment taken in combination with the attached drawings.

DETAILED DESCRIPTION OF THE PREFERRED EMBODIMENT

Figure 1:
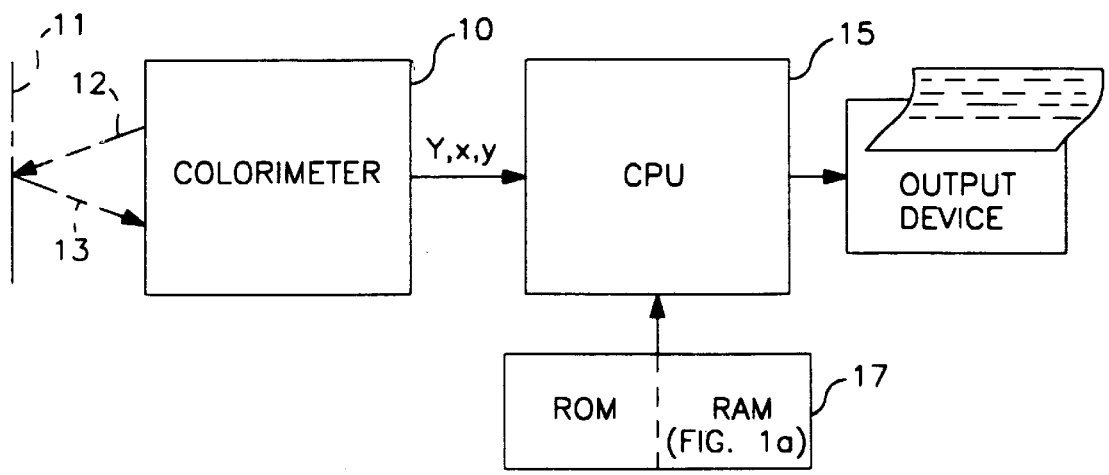
FIG. 1 is a block diagram illustration of an instrument for determining Hunter L, a and b values and for comparing changes in Hunter b to Hunter b changes predetermined to be indicative of bilirubinemia.

Any modern version of two general types of color-measuring instruments, colorimeters and spectrophotometers, are examples of instruments suitable for the skin color measurement according to a preferred embodiment of this invention. The basic components of either type of instrument are a light source, a sample illumination and viewing arrangement, a means of selecting certain wavelengths of light for the measurement, a detector of the light reflected from the sample, and some relatively simple computing capacity. In commercially available instruments the main purposes of the computing capacity are to store and apply calibration information and to calculate various color coordinate for later use. In FIG. 1, a color measuring instrument 10 is illustrated. An individual person's skin 11 is illuminated by the instrument as generally indicated by the broken line arrow 12 and the instrument receives illumination reflected from the skin 11 as generally indicated by the broken line arrow 13. Based on the illumination received by reflection from the skin, the instrument 10 develops the coordinates Y, x and y. In FIG. 1 the instrument 10 is a colorimeter, commercially available and suitable for development of the values Y, x and y.

Another type of instrument that can be used in the skin color categorization method according to this invention is the spectrophotometer that measures the skin reflectance at discrete wavelengths and from these data derives tristimulus values, from which can be computed the Hunter color values used to measure skin color for diagnostic purposes as discussed below.

Important to the use of a commercial colorimeter of the kind employed for the color measurement instrument 10 of FIG. 1 is the calibration of the instrument using a standard. In the early use of an instrument of this kind by the inventors, the "Light Skin" sample from the Macbeth Color Checker, described in the publication of C. S. McCamy, H. Marcus, and J. G. Davidson, "A Color-Rendition Chart," J. Appl. Photogr. Eng. 2, 95–99 (1976) was used. A tile of this approximate color was selected for its greater durability as an instrument standard. It was found, however, that the use of the "Light Skin" painted paper as the primary standard did not adequately avoid the phenomenon known as metamerism, by which objects that look alike (have the same perceived color) under some kinds of light sources or to some observers do not match under other types of light sources or to other observers. By this phenomenon colorimeters may not read their colors the same as the average human observer would under the daylight type light source usually employed for visual observation, hence leading to an error in colorimeter calibration.

As an improved primary standard, the skin of a subject whose skin color measurements were highly reproducible and in the approximate center of the range of skin colors of the human population was selected. The spectral reflectance factors of the skin of this subject were carefully measured on a Macbeth 1500 Plus spectrophotometer (Macbeth, New Windsor, N.Y.); these data are given in column 2 of Table I at the wavelengths listed in column 1. By using well-established techniques of computer color matching, carried out on an ACS 1800 system equipped with an ACS SpectroSensor II color measuring instrument (Datacolor International, Lawrenceville, N.J.) a colorant formulation matching this skin color was developed. The spectral reflectance factors for this match are given in column 3 of Table I. It may be seen that the data closely match those of column 2, indicating the absence of metamerism. Calculations according to the CIE 1976 CIELAB system showed that the two data sets match to within 0.27–0.36 units, less than can be perceived by human color vision, for daylight, incandescent light, and cool white fluorescent light, the three most commonly used light sources for the proposed applications.

The above-mentioned formulation was made up in a stable, durable material, and tiles were prepared as instrument standards. The spectral reflectance factors of one of these tiles are given in column 4 of Table I. It was found, however, that the improvement in calibration resulted in color coordinates that were significantly different from those obtained in the many studies made with the earlier system. A decision was made to adjust the calibration values of the new tiles in order to achieve consistent results between the new and old methods of calibration. Column 5 of Table I gives the adjusted set of spectral reflectance factors for the tile of column 4. The CIE and Hunter color coordinates, the measurement with the specular component excluded and calculated for CIE standard illuminant C and the 1931 2° CIE standard observer, are also tabulated for each of the samples in the table.

TABLE I

| Wavelengths nm. | Skin Standard | Formulation | Tile, correct | Tile, adjusted |
|---|---|---|---|---|
| 400 | 19.03 | 20.70 | 21.51 | 16.67 |
| 420 | 18.96 | 20.69 | 21.10 | 16.93 |
| 440 | 21.53 | 21.68 | 20.99 | 17.65 |
| 460 | 25.36 | 24.43 | 23.27 | 20.56 |
| 480 | 28.06 | 29.30 | 27.82 | 25.67 |
| 500 | 30.13 | 30.77 | 29.03 | 27.94 |
| 520 | 31.19 | 31.31 | 29.38 | 28.24 |
| 540 | 30.01 | 30.84 | 28.48 | 27.59 |
| 560 | 31.41 | 30.76 | 28.22 | 27.33 |
| 580 | 32.85 | 34.01 | 31.49 | 30.12 |
| 600 | 44.37 | 43.54 | 42.58 | 40.52 |
| 620 | 51.24 | 51.57 | 51.27 | 47.93 |
| 640 | 54.56 | 55.09 | 55.56 | 51.10 |
| 660 | 57.09 | 57.60 | 59.22 | 53.82 |
| 680 | 58.67 | 60.41 | 61.82 | 56.55 |
| 700 | 59.95 | 62.69 | 63.93 | 56.87 |
| X | 37.14 | 37.28 | 36.14 | 33.76 |
| Y | 34.66 | 34.59 | 33.07 | 31.53 |
| Z | 28.50 | 28.54 | 27.63 | 24.20 |
| x | 0.3703 | 0.3702 | 0.3732 | 0.3732 |
| y | 0.3456 | 0.3464 | 0.3415 | 0.3523 |
| L | 58.87 | 59.07 | 57.51 | 56.15 |
| a | 9.31 | 9.02 | 11.54 | 9.05 |
| b | 12.51 | 12.70 | 11.77 | 13.75 |

With a suitable standard, basically, calibration is carried out by forcing the colorimeter 10 to give the desired color coordinates Y, x and y mentioned above, while utilizing the colorimeter with the standard tile chosen. The method of calibration is known for particular instruments and follows a series of steps prescribed by the manufacturer that need not be detailed here.

In skin color testing, prior to each test of a subject, each test site is cleansed. A cleansing agent such as isopropyl alcohol, which leaves behind no coloration, is suitable. The site is well dried to avoid any wetness which may interfere with the reflection of light from the skin 11 to the instrument 10. In all cases of testing, with the instrument correctly calibrated, the measuring head or instrument orifice is placed against the test site to be measured. Care is taken to avoid the admission of ambient light to the instrument. Pressing the head firmly against the test site prevents the entry of ambient light. Additionally, it was determined that best results are obtained if one removes the instrument from the test site briefly, between illuminations. This can be provided for in software by a conventional delaying routine and, if desired, with an appropriate display instructing the user to remove the instrument briefly well away from the skin.

In a colorimeter of the type shown in FIG. 1, at block 10 the instrument has an internal microprocessor or other computing capability so that it is able to develop the color coordinates Y, x and y from the measured values X, Y and Z (Y being the same in each case). Certain colorimeters develop the Hunter color coordinates L, a, and b. Since the degree of computation that the color measuring device 10 (i.e. colorimeter or spectrophotometer) internally performs varies, the manner of calculating the Hunter values from the tristimulus coordinates is useful to an understanding and practice of the invention and will enable correct use of a CPU by appropriate calculation to perform the invention with any commercially available colorimeter or spectrophotometer. Most modern color measuring instruments begin with measurement of the tristimulus vales X, Y, and Z. From these can be derived the CIE chromaticity coordinates x and y:

$$x=X/(X+Y+Z) \quad (1)$$

$$y=Y/(X+Y+Z) \quad (2)$$

The instrument 10 of FIG. 1 outputs the triplet of values x, y and Y as the starting point for further calculations by a central processing unit which can be dedicated microprocessor circuitry or personal computer 15. The remaining two tristimulus values X and Z are available by computation as follows:

$$X=xY/y, \text{ and} \quad (3)$$

$$Z=(1-x-y)Y/y \quad (4)$$

In the preferred embodiment, in any event, the CPU according to FIG. 1 develops the Hunter value b discovered in accordance with this invention to be capable of use to detect and monitor hyperbilirubinemia. The Hunter b value is one of three values derived by Richard S. Hunter in 1958. Richard S. Hunter, "Photoelectric Color Difference Meter," J. Opt. Soc. Am. 48, 985–995 (1958). The equations for these are:

$$L=10(Y)^{1/2} \quad (5)$$

$$a=17.5(1.02X-Y)/Y^{1/2} \quad (6)$$

$$b=7.0(Y-0.847Z)/Y^{1/2} \quad (7)$$

where L is a lightness coordinate whose values coorelate better with the visual perceptions of the lightness of object colors than do values of Y; a is a coordinate denoting redness or greenness, for which positive values denote that the color is red rather than its opponent color green, and negative values of a denote the opposite; and b is a yellowness-blueness coordinate, for which positive values denote that the color is yellow rather than the opponent color blue, and negative values of b denote the opposite. For yellow colors, starting with a=b=0 and an appropriate high value of L, which would be a light grey, increasing positive values of b result in a series of colors that may be described as light yellowish grey, pale yellow, light yellow, brilliant yellow and vivid yellow, in turn. Thus b is a measure of the "intensity" of the yellow color.

Historically, all three Hunter values, a, b and L, have been utilized to describe a color. The inventors have determined that one can use the Hunter skin lightness measure L and comparative determinations of the Hunter value b developed at time intervals to measure the jaundice that is symptomatic of hyperbilirubinemia and by that measurement of jaundice detect the presence or absence of the ailment. The coordinate b provides a reliable measure of the yellow undertone of the color of human skin. In the particular arrangement of FIG. 1, wherein the colorimeter 10 produces the values Y, x, y, the computer 15 derives the Hunter values L and b. The Hunter lightness skin color characteristic L affects the amount of increase in the yellow measure Hunter b that indicates hyperbilirubinemia. Following the procedure represented in FIG. 2, steps 1 to 4 and preferably using an averaging technique described below, a newborn is measured, preferably within 2–6 hours of birth, to establish the initial, baseline values of Hunter L and b, $L_0$ and $b_0$. The values are recorded, step 4, for example by placement in machine memory 17. (A baseline Hunter a, $a_0$, may be calculated at this time, too, for the purposes explained below.) Thereafter, again preferably using the averaging technique, throughout the next several days, Hunter L and b are measured at intervals as represented by step 5 of FIG. 2. L is compared to the value originally measured as indicated at step 6. It should not vary more than 3 to 5 points, (depending on the range of L being measured) or the test is discontinued as at step 7. Otherwise, Hunter b is compared at step 8 to the baseline value established shortly after birth. As determined at step 9, if at any time Hunter b increases two points or more for darker skins with L values at or below approximately 51 or three points or more for lighter skins with L values above approximately 51, then hyperbilirubinemia is indicated and phototherapy, the usual treatment for this condition, may be prescribed. Alternatively, a blood test may be conducted to confirm the diagnosis before beginning phototherapy. Hunter b increases of one to two points for L values at or below approximately 51 and Hunter b increases of two or three points for L values above approximately 51 can be used as red flags or warning signs requiring closer monitoring.

When the measured value of Hunter L at any time is found to have varied more than 3–5 points the test procedure is suspect and the test may be discontinued. Hunter L variations of this magnitude do not ordinarily occur in skin color measurement. The test should be repeated and if the discrepancy is not eliminated then the comparison of Hunter b values should not be relied upon for a determination of the presence or absence of hyperbilirubinemia.

During phototherapy too, the testing procedure according to this invention can be used. Continued monitoring of Hunter L and b in the above manner can be utilized until Hunter b is within two points of its baseline value for subjects whose skin lightness value L is below a particular L value or within three points of its baseline for subjects when L is above that value. An L value of approximately 51 has been found approximate for this purpose.

Figure 3:
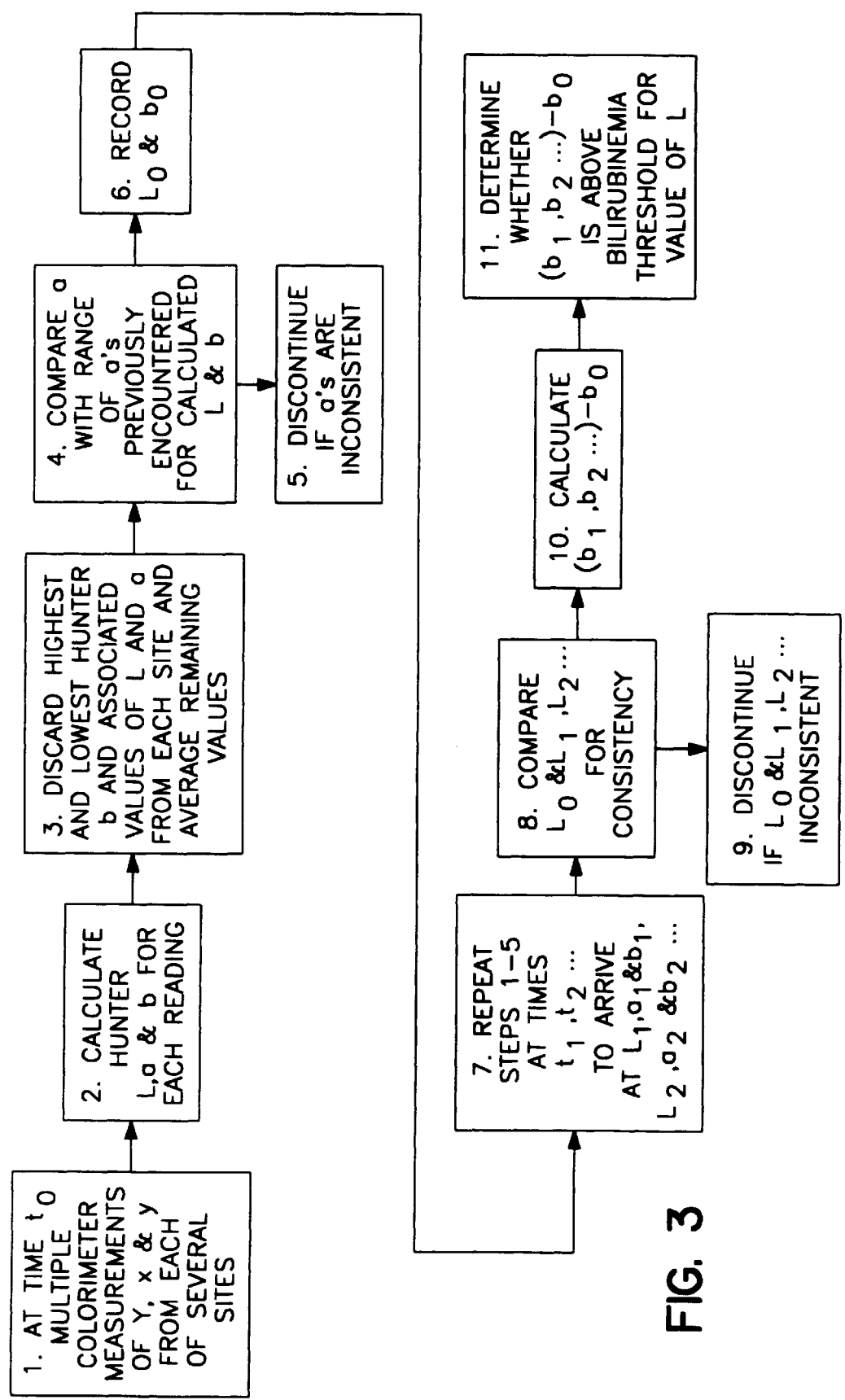
FIG. 3 is a schematic illustration in block diagram form illustrating the steps in the process of monitoring an infant for hyperbilirubinemia based on Hunter b including measuring and reviewing Hunter a as well as Hunter b and L.

Although it has not been found to affect the measurement of Hunter b or the reliability of the use of Hunter L and b to diagnose hyperbilirubinemia, it has been the inventor' practice to require measurement preferably of Hunter a at each testing. Again the averaging technique is preferably used as described below. Based upon the testing of the skin color of several million individuals, the inventors have identified some 210 broad categories of skin coloration. That is to say, 210 broad ranges of Hunter L, a and b have been identified. Hunter L and b values for each of these categories are shown in Table II, Appendix A hereto. Table III, below, provides the ranges of Hunter a reasonably to be expected. For certain values of L, Hunter a above a particular value has never been observed. Should the test indicate a Hunter a outside any previously observed range for a particular L and b, this would be taken as at least an indication of error in testing. This occurrence is represented at steps 4 and 5 of FIG. 3, which drawing figure represents the steps in the hyperbilirubinemia test that includes the measurement and comparison of Hunter a. If retesting does not result in a value of Hunter a consistent with previous experience, then the use of Hunter L and b as a test for hyperbilirubinemia in this instance is discontinued.

TABLE III

| If Hunter L values are: | Then Hunter a values are: |
|---|---|
| 24 (or less) to 44 | 4 to 16 |
| 45 to 54 | 4 to 18 |
| 55 to 59 | 5 to 25 |
| 60 to 71 (or more) | 6 to 30 |

Figure 2:
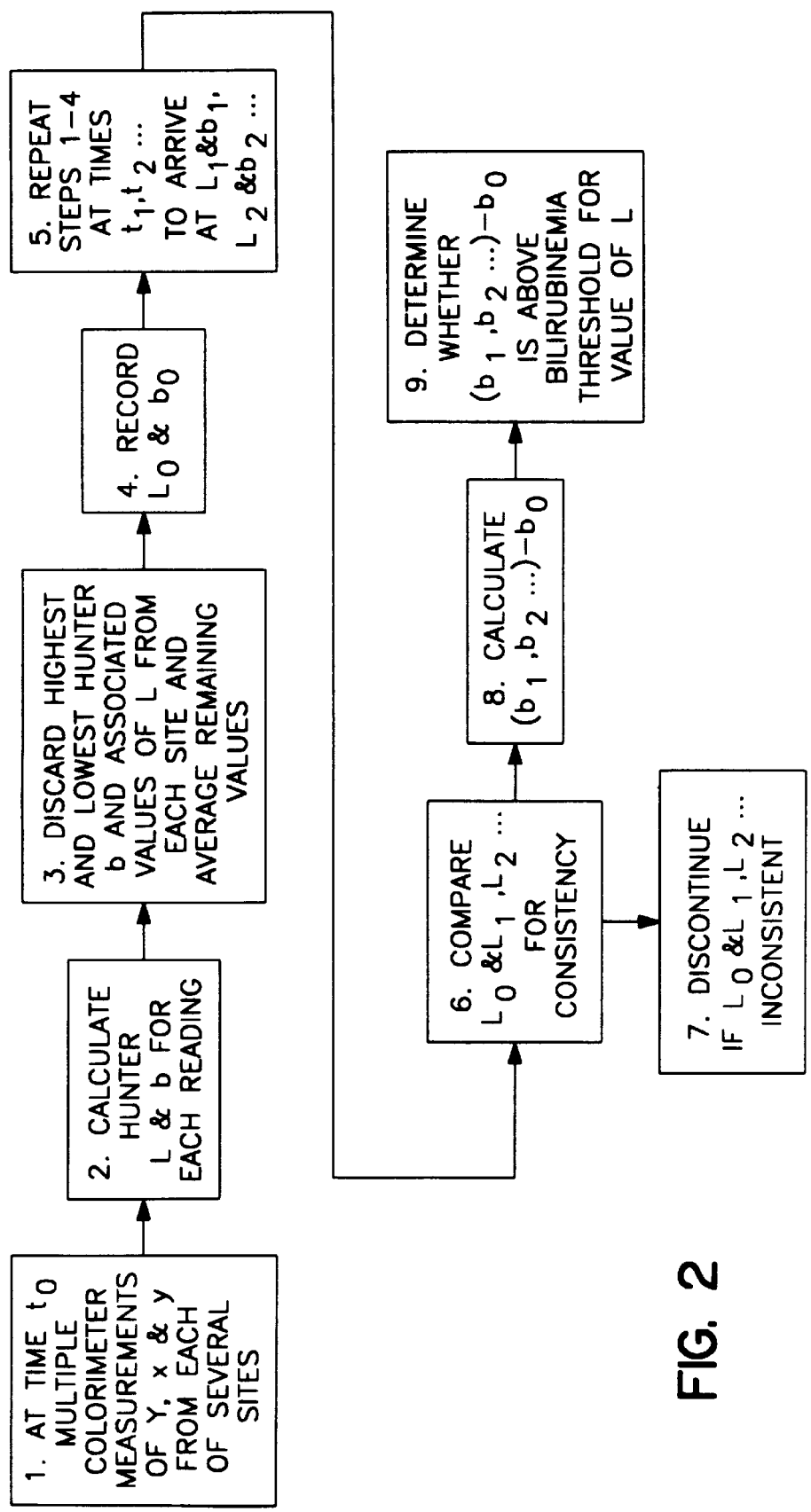
FIG. 2 is a schematic illustration in block diagram form illustrating the steps in the process of monitoring an infant for hyperbilirubinemia based upon changes in Hunter b in skin color and including measuring and reviewing Hunter b and L.

For greater accuracy, multiple Y, x and y readings are made with the colorimeter 10 at several different sites, for example at one or more locations on some or all of the subject's forehead, cheek, chest and back, as suggested in the steps of the method outlined in FIG. 2. In a preferred embodiment 5 or 6 readings at 5 different sites are made. Hunter b and L values are calculated for each reading. The high and low values of b and associated values of L from each site are discarded, the computer 15 then averages all of the remaining values of Hunter b and L. The average b and L thus calculated are then used as the Hunter b and L values in the previously described testing for bilirubinemia.

Some variation of b value occurs in dependence on the body location where readings are taken. Consistently averaging the values of L and b calculated from measurements taken at the same several locations on each individual can be used to eliminate any uncertainty resulting from such variations.

A hospital's measure of serum bilirubin typically uses a scale different from the measure of Hunter b detected by the above procedure. In extensive tests at one hospital, a linear relation was observed between serum bilirubin measured using the hospital's scale and the Hunter b measurement according to the invention. In that hospital 12 was the serum bilirubin value that signalled monitoring or treatment of hyperbilirubinemia.

Correlation between Hunter b and the hospital bilirubin count (BRC) was determined to be in accordance with the following equation:

$$BRC = 2.5([\{47/L\}^{1/2} b] - 6.8) \quad (8)$$

where BRC equals the hospital bilirubin count, the number 47 is the average L for the entire database gathered over the course of research, and L and b are the average Hunter values determined as described above.

The term in braces modifies b according to the value L relative to its average, in this case 47, according to a square root (superscript ½) function. It may be easier to understand the above equation if it is written another way. If the modified b (in square brackets) is called MODB:

$$MODB = 6.8 + 0.4\, BRC \quad (9)$$

The numbers 6.8 and 0.4 (=½.5) are, respectively, the intercept and slope of the straight line relation between modified b and BRC. The 6.8 is the value of MODB when BRC=0 and is related to the average baseline skin color. The 0.4 shows how rapidly MODB changes as BRC increases, an increase of 2.5 in BRC raises MODB by one point.

The equation is exemplary only and may vary in detail when applied to a larger database or to bilirubin count values from another hospital since hospitals do not have a standard scale used consistently from one hospital to the next. However, the linear relationship between MODB and BRC indicates relatively straightforward conversion of measured L and b to arrive at a particular hospital's bilirubin count value so that the medical practitioner can employ the optical measurement of jaundice in accordance with this invention in the same way she or he employed bilirubin count previously.

Figure 1A:
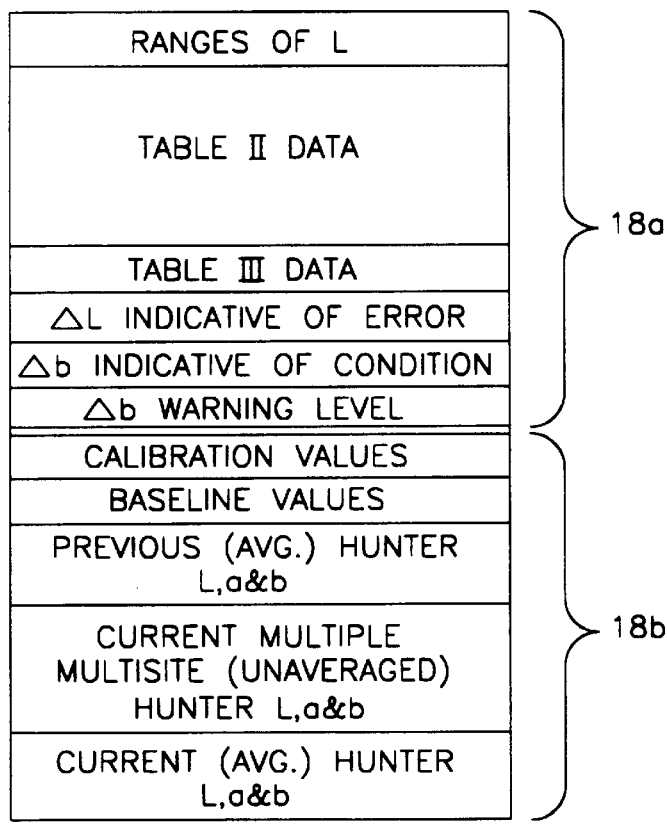
FIG. 1a is a diagrammatic illustration of exemplary memory content in an instrument like that of FIG. 1.

In the system of FIG. 1, following the routine of FIG. 2, from the initial measurement preferably within 2–5 hours of birth, the CPU calculates the initial Hunter values $L_0$, $a_0$ and $b_0$ and stores these in the Baseline Values addresses of the data portion or RAM of memory 17. The data RAM (or nonprogram) portion 18 of the memory 17 is indicated in FIG. 1a. A relatively permanent section 18a of RAM 18 stores the data of Table II (and Table III if Hunter a is to be checked) and data such as the ranges of L that establish categories of skin coloration for which varying Hunter b value changes are significant. A more often revised memory segment stores the results of the measurements performed with the instrument. Based on a relatively straightforward program retained in the permanent ROM memory, from the measurements taken at intervals, the CPU calculates the new values of L and b, retrieves $L_0$ and $b_0$, and subtracts those from the new value $L_1$ and $b_1$. The change in Hunter L and b, $\Delta L$ and $\Delta b$, can be displayed, or preferably, the CPU determines if the change in L indicates an error by comparing the change in L to that value, stored in the RAM 18 of the memory 17, that raises the suspicion of test error. If there is no suspicion of error, then the CPU determines whether an increase in b is above the value, again stored in memory, that indicates monitoring or treatment of hyperbilirubinemia for the particular value of L that has been measured. Similarly, for an infant that has previously been diagnosed with hyperbilirubinemia and is undergoing phototherapy, the same order of decrease to within 2 or 3 points of baseline, depending on L, can indicate recovery and phototherapy may be ended. The CPU memory 17 can be provided with Table II, or another compilation of the categories of skin coloration, which the CPU then can use as a look-up table to determine if Hunter a has a value outside of previously observed ranges for the particular Hunter L and b. Also, if desired, the CPU can calculate the display the hospital's measure of serum bilirubin based upon changes in Hunter b, for example by applying equation 8 above.

Even in the absence of an initial reading, based on observed ranges of skin coloration, measurement of Hunter L and b can warn of the likelihood of hyperbilirubinemia if a Hunter b value is measured that is in excess of Hunter b ordinarily observed for subjects with that value of L. Hunter b values exceeding those ordinarily observed for individuals in a particular range of Hunter L values can be determined by reference to Table II. For example, it will be apparent that no individual whose skin has a Hunter L value between 24 and 26 has measured above 13 in Hunter b. Such a measurement may be used to determine that a blood test is advisable. In all instances, however, even where there has not been a Hunter b baseline established, an increase over time of 2, 3 or more Hunter b points indicates the likelihood of hyperbilirubinemia, and if the change is a decrease, this is indicative of a recovering newborn.

Table IV is an actual set of measurements made on a three day old infant. Using the averaging technique described above, Hunter L of 48.0 and Hunter b of 11.1 is calculated. Converting to the hospital bilirubin count in the equation (9) above, a bilirubin count of 10.5 was calculated.

TABLE IV

|  | L | a | b | Y | x | y |
|---|---|---|---|---|---|---|
| Forehead | 47.6 | 21.6 | 11.6 | 22.9 | 0.411 | 0.333 |
|  | 48.6 | 19.5 | 11.5 | 23.6 | 0.404 | 0.335 |
|  | 48.8 | 21.2 | 11.6 | 23.8 | 0.407 | 0.333 |
|  | 46.7 | 21.6 | 11.6 | 21.8 | 0.413 | 0.333 |
|  | 48.6 | 21.6 | 11.8 | 23.6 | 0.410 | 0.333 |
|  | 48.0 | 22.1 | 11.7 | 23.1 | 0.412 | 0.332 |
| Forehead | 46.4 | 20.5 | 11.2 | 21.5 | 0.409 | 0.333 |
|  | 46.0 | 20.3 | 11.1 | 21.1 | 0.409 | 0.333 |
|  | 47.4 | 21.4 | 11.6 | 22.4 | 0.411 | 0.333 |
|  | 46.1 | 21.4 | 10.7 | 21.2 | 0.409 | 0.330 |
|  | 46.3 | 20.4 | 11.2 | 21.5 | 0.409 | 0.333 |
|  | 46.9 | 20.7 | 11.3 | 22.0 | 0.409 | 0.333 |
| Chest | 50.5 | 16.5 | 11.2 | 25.5 | 0.391 | 0.336 |
|  | 50.9 | 15.3 | 11.2 | 25.9 | 0.388 | 0.338 |
|  | 50.1 | 17.5 | 11.2 | 25.1 | 0.395 | 0.336 |
|  | 50.7 | 16.9 | 11.2 | 25.7 | 0.392 | 0.336 |
|  | 50.4 | 16.4 | 11.1 | 25.4 | 0.391 | 0.336 |
|  | 50.1 | 17.3 | 11.1 | 25.1 | 0.394 | 0.335 |
| Back | 49.0 | 17.1 | 11.1 | 24.0 | 0.395 | 0.336 |
|  | 48.7 | 16.3 | 11.0 | 23.7 | 0.394 | 0.337 |
|  | 48.3 | 16.6 | 10.6 | 23.3 | 0.393 | 0.335 |
|  | 49.2 | 16.6 | 10.9 | 24.2 | 0.393 | 0.336 |
|  | 49.1 | 18.3 | 11.3 | 24.1 | 0.399 | 0.335 |
|  | 50.0 | 18.0 | 11.4 | 25.0 | 0.397 | 0.336 |
| Back | 46.2 | 15.8 | 10.5 | 21.4 | 0.395 | 0.337 |
|  | 45.3 | 16.5 | 10.2 | 20.5 | 0.397 | 0.335 |
|  | 45.9 | 16.0 | 10.4 | 21.1 | 0.395 | 0.336 |
|  | 45.5 | 14.4 | 10.3 | 20.7 | 0.392 | 0.338 |
|  | 46.3 | 16.1 | 11.0 | 21.4 | 0.398 | 0.339 |
|  | 47.3 | 16.9 | 10.9 | 22.3 | 0.397 | 0.336 |

The invention can afford good evidence of jaundice resulting from medical conditions other than hyperbilirubinemia. Liver disorders in adults and children produce jaundice, for example. These and other skin color characteristics can be factors in diagnosing additional diseases that affect skin color. It has been observed, for example, that at least among dark skinned individuals, such as African Americans or others of African descent, skin color is affected by tuberculosis.

The application of the method and apparatus is not limited to the jaundice-related testing described above. Experiments with rhesus monkeys have shown a correlation between hormone levels and the coloration of the female monkey's very visible reddened hind end. An instrument like that described above was able to distinguish varying levels of reddening in an individual test subject's posterior using of Hunter a, and Hunter L in a similar fashion to that described above. The hormone level of the subject was thus indicated by the methods and apparatus of this invention.

Successful experimentation has begun on the evaluation of the condition of laboratory mice based upon the use of Hunter a and Hunter L in a similar fashion to that described above.

Table V, Appendix B, is a broad categorization of human hair coloration. Departure of an individual test subject's hair coloration from a baseline measure can be an indication of a change in the hair or of greying. In addition to diagnostic use, test procedures and instruments according to this invention can be used to determine how to restore the hair to its natural color, or with reference to the categories of Table V, hair that has changed in color by greying or by bleaching or dying can be restored to a more natural appearance, whether the test subject's original coloring or a chosen color consistent with the limitation of the categories identified in Table V.

In much the same way tooth coloration can be assessed by this invention and the techniques described can be used to arrive at a natural coloring of replacement dental work consistent with existing or replacement teeth.

Plant and crop specimens are good candidates for the applicaiton of the procedures and apparatus of the invention. For example, conditions leading to the degradation of grain stored in silos in observable based upon color change. Determination of these conditions by instrument is made possible by the techniques of the present invention and this opens the way to automated monitoring for this purpose. Soil samples from oil spills when measured by these procedures and apparatus indicate the degree of soil contamination by oil or gasoline. Testing of such soil contamination has ben successfully conducted. Biological test subjects of a great variety can be tested by means of the present invention.

From the foregoing it should be apparent that the methods and apparatus described are exemplary and not intended to limit the scope of protection of the invention as set forth in the appended claims.

What is claimed is:

1. An apparatus for detecting a condition in a test subject, which condition includes a symptomatic, detectable change in the test subject's coloration; said apparatus comprising:

(a) an instrument for measuring a value of at least one color factor in the test subject'coloration, said color factor being dependent, at least in part, on relative content of one or more colors in said coloration;

(b) means for storing a value related to the at least one color factor; and (c) an computational device communicably linked with said instrument; said computational device comprising means for comparing the value related to the at least one color factor measured, with a pre-established range of such value evidencing either the presence or absence of the condition.

2. The apparatus according to claim 1, wherein the value related to the at least one color factor is the difference between values of the at least one color factor measured at first and second points in time.

3. The apparatus according to claim 1, wherein the value related to the at least one color factor is a value substantially that of the said color factor.

4. An apparatus for detecting a condition in a test subject, which condition includes a symptomatic coloration; said apparatus comprising:

(a) an instrument for measuring a value of at least one color factor in said test subject's coloration, said color factor being dependent on said coloration and being correlatable to a measure of said condition that has clinical utility, and (b) a computational device communicably linked to said instrument for comparing the measured value of said color factor with a predetermined range of values of said color factor to determine whether said measured value of said color factor evidences said condition in said test subject.

5. The apparatus according to claim 4, wherein said instrument measures a color factor correlatable, in test subjects having colorations of substantially varying degrees of lightness or darkness, to a measure of said condition that has clinical utility.

6. The apparatus according to claim 4, wherein said computational device compares the measured value of said color factor with a range of acceptable values of said color factor that is indicative of the presence or absence of said condition in said subject to determine if the measured value of said color factor lies inside or outside the range.

7. The apparatus according to claim 4, wherein said instrument further measures a color factor which is color factor Hunter b or a color factor which is substantially that of color factor Hunter b in said coloration of said test subject and said computational device compares the measured value of said color factor of said test subject with a range of values of said color factor associated with said at least one color factor in subjects other than said test subject, said subjects being comparable with said test subject in said at least one color factor of coloration.

8. The apparatus according to claim 4, wherein said computational device compares the measured value of said color factor with a range of values of said color factor characteristic of subjects without said condition.

9. The apparatus according to any one of claims 4, 5, 6 and 8, wherein said at least one color factor comprises one or more color factors correlatable either alone or in combination to serum bilirubin count (BRC).

10. The apparatus according to claim 9, wherein the one or more color factors have values that are or substantially are those of Hunter b and Hunter L in the skin coloration of the test subject, and that convert to BRC substantially pursuant to the relationship $$BRC=2.5\ ([\{47/L\}^{1/2}b]-6.8),$$

where BRC is serum bilirubin count, L is the value that is or substantially is that of Hunter L, and b is the value that is or substantially is that of Hunter b.

11. The apparatus according to any one of claims 4, 5, 6, 8, wherein said value of said at least one color factor is or substantially is that of Hunter b, the test subject is an infant human being, and the measure of said condition that has clinical utility is serum bilirubin count (BRC), and a lightness-dependent function of Hunter b or substantially Hunter b (MODB) has a predetermined straight line relationship to BRC.

12. The apparatus according to claim 11, wherein $$MODB=(46/L)^{1/2}b$$

where b is the value that is or substantially is that of Hunter b, 47 is the average of a value that is or substantially is that of Hunter L in the population of infants, and L is the value of a color factor that is or substantially is that of Hunter L;

said straight line relationship to BRC has an intercept of substantially 6.8 and a slope of substantially 0.4 such that $$MODB=6.8+0.4\ BRC;\ \text{and}$$

whereby the relation between the value that is substantially that of Hunter b and BRC is:

$$BRC=2.5\ ([\{47/L\}^{1/2}b]-6.8).$$

13. The apparatus according to claim 4, further comprising means for storing ranges of values of a lightness measure color factor, said lightness measure color factor being substantially that of color factor Hunter L, in association with ranges of a color factor substantially that of color factor Hunter a, the relationship between the lightness measure color factor value ranges and associated color factor values being substantially equivalent to the following:

| Hunter L | Hunter a |
|---|---|
| 24 (or less) to 44 | 4 to 16 |
| 45 to 54 | 4 to 18 |
| 55 to 59 | 5 to 25 |
| 60 to 71 (or more) | 6 to 30. |

14. The apparatus according to claim 4, wherein said instrument includes means for measuring the value of a color factor that is dependent on relative content of opponent colors in said coloration.

15. The apparatus according to claim 4, wherein said instrument includes means for measuring the value of a color factor that is dependent on lightness of the coloration of said test subject.

16. An apparatus for detecting a condition of a test subject based on coloration of said test subject; said apparatus being characterized by:

(a) an instrument for measuring a value of at least one color factor in said coloration of said test subject, said color factor being substantially that of color factor Hunter b; and (b) a computational device communicably linked to said instrument, said computational device comprising means for comparing the measured value of said color factor with a range of acceptable values of said color factor that are indicative of the presence or absence of the condition in a subject to determine if the measured value of said color factor lies inside or outside the range.

17. The apparatus according to claim 4, or 16, further comprising means for establishing a plurality of coloration classes in each of which a preestablished magnitude of change in value of said color factor is indicative of said condition.

18. The apparatus according to claim 17, wherein said plurality of coloration classes are colorations within varying ranges of lightness.

19. The apparatus according to any one of claims 4, 5, or 16, wherein said coloration is skin coloration and said condition is hyperbilirubinemia.

20. An apparatus for evaluating a test subject based on the coloration of said test subject in the visible spectrum, said apparatus comprising an instrument for measuring a value of a first color factor in said test subject's coloration, said first color factor being dependent on the lightness of the coloration of said test subject, and a value of at least one further color factor in said test subject's coloration in the visible spectrum, said further color factor being dependent on the relative content of opponent colors in the coloration of said test subject; and a computational device communicably linked to said instrument; at least one of said color factors measured by said instrument correlating to a predetermined measure of coloration having established laboratory utility.

21. The apparatus according to claim 20, wherein said computational device comprises means for comparing the measured values of said first and said further color factors with a stored range of values of said color factors that are found in the colorations of test subjects other than said test subject, to determine where within said range the measured values of said color factors lie.

22. The apparatus according to claim 4, 16, or 20, wherein said instrument includes means for measuring the value of each said color factor at different locations on said test subject.

23. The apparatus according to claim 4, or 20, wherein said instrument includes means for measuring a value of a color factor that is dependent on lightness of the coloration of the test subject and that modifies the relative content of the opponent colors in said coloration.

24. The apparatus according to claim 4, or 20, wherein said instrument includes means for measuring the value of a color factor that is dependent on relative content of blue and yellow in said coloration.

25. The apparatus according to claim 4 or 20, wherein said instrument includes means for measuring the value of a color factor that is dependent on relative content of green and red in said coloration.

26. The apparatus according to claim 4, or 20, wherein said instrument includes means for measuring the value of a color factor that is dependent on yellowness of said coloration of said test subject.

27. The apparatus according to claim 4 or 20, wherein said instrument includes means for measuring the value of a color factor which is color factor Hunter b or a color factor which is substantially that of color factor Hunter b.

28. The apparatus according to claim 4 or 20, wherein said instrument includes means for measuring the value of a color factor that is dependent on redness of said coloration of said test subject.

29. The apparatus according to claim 4 or 20, wherein said instrument includes means for measuring the value of a color factor that comprises a first function weighted in a first portion of the spectrum and a second function weighted in a second portion of the spectrum; the color factor being further dependent on lightness of the coloration of the test subject.

30. The apparatus according to claim 29, wherein the coloration is skin coloration and the condition is hyperbilirubinemia; said apparatus further comprising means for comparing the values of said color factor measured with coloration classes that include a first class of skin coloration having a value of a color factor which is substantially that of a color factor Hunter L value at or below substantially 51 and a second class of skin coloration having a value of a color factor which is substantially that of a color factor Hunter L value above substantially 51 to determine whether said value is indicative of hyperbilirubinemia.

31. The apparatus according to claim 4 or 20, wherein said instrument includes means for measuring the value of a first color factor which is substantially that of color factor Hunter b, said instrument further comprising means for measuring a value of a further color factor which is substantially that of color factor Hunter a; and said computational device comprises means for comparing the measured value of said further color factor with a range of values of said further color factor to determine whether the measured value of said further color factor lies within an acceptable range.

32. The apparatus according to claim 20, wherein said instrument includes means for measuring the value of a color factor which is substantially that of color factor Hunter b and said lightness measure color factor value ranges are ranges of values of a color factor which is substantially that of color factor Hunter L, the instrument further comprising means for measuring a value of said color factor which is substantially that of color factor Hunter L of said subject's coloration.

33. The apparatus according to claim 4 or 20, wherein said measuring instrument includes means for measuring a color factor which is substantially that of color factor Hunter a.

34. The apparatus according to any one of claims 4, 16 or 20, wherein said instrument includes means for making a set of multiple measurements of each said color factor value and for averaging each set of multiple measurements.

35. The apparatus according to claim 34, wherein said means for making a set of multiple measurements and averaging each set of multiple measurements comprises means for making a set of at least five measurements of the color factor value and averaging each set of multiple measurements.

36. The apparatus according to claim 35, wherein said means for making a set of multiple measurements and averaging each set of multiple measurements comprises means for discarding high and low values of each set of multiple measurements prior to averaging.

37. The apparatus according to any one of claims 4, 5, 16 or 20, wherein said apparatus includes means for detecting a condition that causes jaundice in a human child or adult test subject.

38. The apparatus according to any one of claims 4, 5, 16 or 20, wherein said apparatus includes means for detecting a condition in a biological test subject.

39. The apparatus according to claim 38, wherein said apparatus includes means for detecting a condition in a biological test subject that is selected from the group consisting of plants and soil.

40. The apparatus according to claim 38, wherein said apparatus includes means for detecting a condition in a biological test subject that is selected from the group consisting of tissue, excretions, body fluids, hair and teeth.

41. The apparatus according to any one of claims 4, 5, 16 or 20, wherein said apparatus includes means for detecting a condition in a test subject that is a human infant.

42. The apparatus according to any one of claims 4, 5, 16 or 20, wherein said apparatus includes means for detecting a condition selected from the group consisting of liver disorders, hypertension and tuberculosis.

43. An apparatus for detecting a condition in a test subject, which condition includes a symptomatic, detectable coloration; said apparatus comprising:

(a) an instrument for measuring a value of at least one color factor in the test subject's coloration, said color factor being dependent, at least in part, on relative content of one or more colors in said coloration;

(b) means for storing the value of the at least one color factor; and (c) a computational device communicably linked with said instrument; said computational device further comprising means for comparing said measured value of said at least one color factor with a preestablished measure of color factor values to determine whether said measured value of said color factor evidences said condition in said test subject.

44. An apparatus for detecting a condition in a test subject, which condition includes a symptomatic coloration; the apparatus comprising:

(a) a color measuring instrument for measuring a value in the test subject's coloration of at least one color factor, said color factor being dependent on said coloration and being correlatable, in test subjects having colorations of substantially varying degrees of lightness or darkness, to a measure of the condition that has clinical utility; and (b) means for comparing the measured value of said color factor with a predetermined range of values of the color factor to determine whether said measured value of said color factor evidences said condition in said test subject.

45. The apparatus according to claim 44, wherein:

said at least one color factor is color factor Hunter b or a color factor which is substantially that of color factor Hunter b;

said predetermined range of values comprises recorded values of said color factor associated with at least one other color factor in individuals without said condition; and said comparing means compares the value of said color factor in the skin coloration of the test subject with said predetermined values of said color factor recorded for individuals comparable with the test subject in said other color factor of skin coloration.

46. The apparatus according to claim 43 or 44, wherein said comparing means further comprises means for comparing the measured value of said color factor with a range of values of said color factor that is indicative of either the presence or absence of the condition in a subject to determine if the measured value of said color factor lies inside or outside the range.

47. The apparatus according to claim 46, wherein said at least one color factor of the test subject's coloration is dependent on redness of the coloration of the test subject.

48. The apparatus according to claim 43 or 44, wherein said at least one color factor is color factor Hunter b or a color factor which is substantially that of color factor Hunter b and wherein said comparing means further comprises:

means for storing the value of said color factor in the coloration of the test subject as measured at a first point in time;

means for determining any difference between said stored measured value of said color factor and one or more subsequent measurements of said color factor in the coloration of the test subject; and means for comparing said difference to a range of values to determine whether a change in color factor value inside or outside said range is present, indicative of either the presence or absence of the condition.

49. The apparatus according to claim 48, wherein the subject is an infant human being and said value substantially that of Hunter b measured at a first point in time comprises a value of said color factor measured within two to five hours of the infant's birth.

50. The apparatus according to claim 43 or 44, wherein said at least one color factor is color factor Hunter a or a color factor which is substantially that of color factor Hunter a.

51. The apparatus according to claim 43, or 44, wherein said color factor is dependent on relative content of blue and yellow in said coloration.

52. The apparatus according to claim 43 or 44, wherein said color factor is dependent on relative content of green and red in said coloration.

53. The apparatus according to claim 43 or 44, wherein said color factor is dependent on yellowness of the coloration of the test subject.

54. The apparatus according to claim 43 or 44, wherein said color factor is color factor Hunter b or a color factor which is substantially that of color factor Hunter b.

55. The apparatus according to claim 43 or 44, wherein said color factor value comprises a first function weighted in a first portion of the spectrum and a second function weighted in a second portion of the spectrum, the color factor being further dependent on lightness of the coloration of the test subject.

56. The apparatus of claim 43 or 44, wherein:

said at least one color factor is color factor Hunter b or a color factor which is substantially that of color factor Hunter b;

said color measuring instrument includes means for measuring a value of a second color factor, said second color factor being color factor Hunter a or a color factor which is substantially that of color factor Hunter a; and said comparing means includes means for comparing the measured value of said second color factor with an acceptable range of values of said second color factor to determine whether the measured value of said second color factor lies within said acceptable range.

57. An apparatus for detecting the condition of a test subject based on coloration of said test subject; the apparatus comprising:

(a) a color measuring instrument for measuring the value of at least one color factor in said coloration of the test subject, said color factor being color factor Hunter b; and (b) means for comparing the measured value of said color factor Hunter b with a range of values of Hunter b that are indicative of either the presence or absence of the condition in a subject to determine if the measured value of said color factor lies inside or outside the range.

58. An apparatus for detecting a condition in a test subject, which condition includes a symptomatic coloration; the apparatus comprising:

(a) a color measuring instrument for measuring the value of at least one color factor which is color factor Hunter b or a color factor which is substantially that of color factor Hunter b in the test subject's coloration, said color factor being dependent on said coloration;

(b) means for comparing the measured value of said color factor with a predetermined range of values of the color factor to determine whether said measured value of said color factor evidences said condition in said test subject;

(c) means for determining any difference between the measured value of said color factor and subsequent measurements of said color factor in the coloration of the test subject; and (d) means for comparing said difference to a range of values of change of said color factor to determine whether a change in value of said color factor inside or outside said range is present, indicative of either the presence or absence of the condition.

59. The apparatus according to claim 44, 51, or 58, wherein said color factor is further dependent on lightness of the coloration of the test subject.

60. The apparatus according to claim 44, 57 or 58, wherein said color factor is color factor Hunter b or a color factor which is substantially that of color factor Hunter b, and the predetermined range of values is a range of values of said color factor.

61. The apparatus according to claim 58, wherein said color measuring instrument includes means for averaging a set of multiple measurements of the color factor value.

62. The apparatus according to claim 58, wherein said color measuring instrument is adapted to measure the value of said color factor at different locations on the test subject.

63. The apparatus according to claim 43, 44, 57 or 58, further comprising means for storing a plurality of previously established coloration classes in each of which a preestablished magnitude of change in value of said color factor is indicative of said condition.

64. The apparatus according to claim 63, wherein said coloration classes are determined by ranges of Hunter L values; said ranges of Hunter L values being bounded by at least one of the Hunter L values substantially as follows:

Hunter L=27, 30, 33, 36, 39, 42, 45, 48, 51, 54, 57, 60, 63, 66 and 69.

65. The apparatus according to any one of claims 43, 44, 57 or 58, further comprising means for storing a previously established range of values of the color factor characteristic of subjects without said condition.

66. The apparatus according to any one of claims 43, 44, 57 or 58, wherein said condition to be detected is a condition that causes jaundice in a human child or adult test subject.

67. The apparatus according to any one of claims 43, 44, 57 or 58, wherein the coloration is skin coloration, and the condition to be detected is hyperbilirubinemia.

68. The apparatus according to any one of claims 43, 44, 57 or 58, wherein the test subject comprises a biological test subject.

69. The apparatus according to claim 68, wherein the biological test subject is a human or animal test subject.

70. The apparatus according to claim 69, wherein the test subject is a human infant.

71. The apparatus according to claim 68, wherein the biological test subject is selected from the group consisting of plants and soil.

72. The apparatus according to claim 68, wherein the biological test subject is selected from the group consisting of tissue, excretions, body fluids, hair and teeth.

73. The apparatus according to any one of claims 43, 44, 57 or 58, wherein said condition is selected from the group consisting of liver disorders, hypertension, and tuberculosis.

74. In an apparatus for determining a color characteristic, the improvement comprising:
(a) means for compiling a group of lightness measure color factor value ranges, said lightness measure color factor comprising a color factor which is color factor Hunter L or a color factor which is substantially that of color factor Hunter L; and
(b) means for associating with each lightness measure color factor value range a value of at least one further color factor for use in comparison with a measurement of the value of said at least one further color factor in the coloration of a test subject having a lightness measure color factor value in a corresponding range, said at least one further color factor being color factor Hunter a or a color factor which is substantially that of color factor Hunter a, and the relationship between said lightness measure color factor value ranges and said associated color factor values being substantially as follows:

| Hunter L | Hunter a |
|---|---|
| 24 (or less) to 44 | 4 to 16 |
| 45 to 54 | 4 to 18 |
| 55 to 59 | 5 to 25 |
| 60 to 71 (or more) | 6 to 30 |

75. An apparatus for evaluating a test subject based on the coloration of said test subject, the apparatus comprising:
(a) a color measuring instrument for measuring a value of a first color factor in said test subject's coloration, said first color factor being dependent on the lightness of the coloration of said test subject, and for measuring a value of at least one further color factor in said test subject's coloration, said further color factor being dependent on the relative content of opponent colors in the coloration of said test subject, at least one of said measurements arriving at a value of said respective color factor that correlates to a measure of coloration having established laboratory utility; and means for comparing the measured values of said first color factor and said at least one further color factor with a range of values of said color factors that are found in the colorations of subjects other than said test subject, to determine where within said range the measured values of said color factors lie.

76. The apparatus according to claim 75, wherein the test subject is selected from the group consisting of skin, tissue, excretions, bodily fluids, hair and teeth.

77. The apparatus according to claim 75, wherein said at least one further color factor is dependent on relative content of blue and yellow in said coloration.

78. The apparatus according to claim 75, wherein said at least one further color factor is dependent on relative content of red and green in said coloration.

79. The apparatus according to claim 75, wherein said color measuring instrument includes means for measuring the values of said first color factor and said at least one further color factor at different locations on the test subject.

80. The apparatus according to claim 75, wherein said color measuring instrument further comprises means for averaging a set of multiple measurements of the values of each said first color factor and said at least one further color factor.

81. An apparatus for detecting a condition in a test subject, which condition includes a symptomatic, detectable change in the test subject's coloration; said apparatus comprising:
(a) an instrument for measuring a value of at least one color factor in the test subject's coloration, said color factor being dependent, at least in part, on relative content of one or more colors in said coloration;
(b) means for storing the value of he at least one color factor; and
(c) a computational device communicably linked with said instrument; said computational device comprising means for comparing the values of said at least one color factor measured at a first and at least one further point in time to arrive at a value of change in color factor; said device further comprising means for comparing the value of change in color factor with a preestablished measure of color factor value change, stored in said means for storing, evidencing said condition.

82. The apparatus according to claim 81, wherein said instrument includes means for measuring a value of a color factor further dependent on lightness of said coloration.

83. The apparatus according to claim 82, wherein said instrument includes means for measuring a value of a color factor that comprises a first function weighted in a first portion of the spectrum, a second function weighted in a second portion of the spectrum, and a weighting term that is a function of lightness of said coloration and that modifies the value of the color factor.

84. The apparatus according to claim 81, wherein said instrument includes means for measuring a value of a color factor that comprises a first function weighted in a first portion of the spectrum, a second function weighted in a second portion of the spectrum, and a weighting term that is a function of lightness of said coloration and that modifies the value of the color factor.

85. The apparatus according to claim 84 or 83, wherein said color factor comprises a first function weighted in a yellower portion of the spectrum and a second function weighted in a bluer portion of the spectrum.

86. The apparatus according to claim 81, wherein said value of said at least one color factor in said test subject's coloration measured at said first point of time comprises a baseline measurement made when the symptomatic, detectable change in coloration resulting from the condition is generally not present in a test subject.

87. The apparatus according to claim 81, wherein said test subject is an infant, said condition is hyperbilirubinemia, said value of said at least one color factor in said infant's coloration measured at said first point in time is measured at a time following birth when jaundice resulting from hyperbilirubinemia is generally not present in an infant and said computational device further comprises means for determining whether there has been exhibited a change therein of a predetermined magnitude for that particular infant.

88. The apparatus according to claim 81, wherein said means for storing includes means for storing a plurality of coloration classes in which a predetermined magnitude of a change in value of said at least one color factor is indicative of said condition, said predetermined magnitude indicative of said condition differing from one coloration class to another; and said computational device further comprises means for comparing the values of said color factor measured at said first and said further points in time and determining whether there has been exhibited a change in value of said at least one color factor of a predetermined magnitude evidencing said condition for the particular coloration class of said test subject.

89. The apparatus according to claim 88, wherein said plurality of coloration classes are colorations within varying ranges of lightness.

90. The apparatus according to claim 81, wherein said means for storing includes means for storing a plurality of coloration classes that are colorations within varying ranges of lightness.

91. The apparatus according to any one of claims 81, 82, 84, 83, 86, 87, 88 or 90, wherein said instrument includes means for measuring the value of a color factor that is dependent on relative content of opponent colors in said coloration.

92. The apparatus according to claim 91, wherein said instrument includes means for measuring a value of a color factor that is dependent on lightness of the coloration of the test subject and that modifies the relative content of the opponent colors in said coloration.

93. The apparatus according to any one of claims 86, 87, 88 or 90, wherein said instrument includes means for measuring the value of a color factor that is dependent on lightness of the coloration of said test subject.

94. The apparatus according to any one of claims 81, 82, 84, 83, 86, 87, 88 or 90, wherein said instrument includes means for measuring the value of said color factor at different locations on said test subject.

95. The apparatus according to any one of claims 81, 82, 84, 83, 86, 87, 88 or 90, further comprising means for establishing a plurality of coloration classes in each of which a preestablished magnitude of change in value of said color factor is indicative of said condition.

96. The apparatus according to any one of claims 81, 82, 84, 83, 86, 87, 88 or 90, wherein said instrument includes means for measuring the value of a color factor that is dependent on relative content of blue and yellow in said coloration.

97. The apparatus according to any one of claims 81, 82, 84, 83, 86, 87, 88, or 90, wherein said instrument includes means for measuring the value of a color factor that is dependent on relative content of green and red in said coloration.

98. The apparatus according to any one of claims 81, 82, 84, 83, 86, 87, 88 or 90, wherein said instrument includes means for measuring the value of a color factor that is dependent on yellowness of said coloration of said test subject.

99. The apparatus according to any one of claims 81, 82, 84, 83, 86, 87, 88 or 90, wherein said instrument includes means for measuring the value of a color factor which is color factor Hunter b or a color factor which is substantially that of color factor Hunter b.

100. The apparatus according to any one of claims 81, 82, 84, 83, 86, 87, 88 or 90, wherein said instrument includes means for measuring the value of a color factor that is dependent on redness of said coloration of said test subject.

101. The apparatus according to any one of claims 81, 82, 84, 83, 86, 87, 88 or 90, wherein said instrument include means for measuring the value of a color factor that comprises a first function weighted in a first portion of the spectrum and a second function weighted in a second portion of the spectrum; the color factor being further dependent on lightness of the coloration of the test subject.

102. The apparatus according to claim 101, wherein the coloration is skin coloration, the condition is hyperbilirubinemia; and said apparatus further comprises means for comparing the values of said color factor measured with coloration classes that comprise a first class of skin coloration having a value of a color factor which is color factor Hunter L or a color factor which is substantially that of color factor Hunter L at or below substantially 51 and a second class of skin coloration having a value of color factor Hunter L or a color factor which is substantially that of color factor Hunter L above substantially 51 to determine whether said value is indicative of hyperbilirubinemia.

103. The apparatus according to any one of claims 81, 82, 84, 83, 86, 87, 88 or 90, wherein said instrument includes means for measuring the value of a first color factor which is color factor Hunter b or a color factor which is substantially that of color factor Hunter b, the apparatus further comprises means for measuring a value of a second color factor which is color factor Hunter a or a color factor which is substantially that of color factor Hunter a; and said computational device comprises means for comparing the measured value of said second color factor with a range of values of said second color factor to determine whether the measured value of said second color factor lies within an acceptable range.

104. The apparatus according to any one of claims 81, 82, 84, 83, 86, 87, 88 or 90, wherein said measuring instrument includes means for measuring a color factor which is color factor Hunter a or a color factor which is substantially that of color factor Hunter a.

105. The apparatus according to any one of claims 81, 82, 84, 83, 86, 87, 88 or 90, wherein said instrument includes means for making a set of multiple measurements of the color factor value and averaging each set of multiple measurements.

106. The apparatus according to claim 105, wherein said means for making a set of multiple measurements and averaging each set of multiple measurements comprises means for making a set of at least five measurements of the color factor value and averaging each set of multiple measurements.

107. The apparatus according to claim 106, wherein said means for making a set of multiple measurements and averaging each set of multiple measurements comprises means for discarding high and low values of each set of multiple measurements prior to averaging.

108. The apparatus according to claim 105, wherein said means for making a set of multiple measurements and averaging each set of multiple measurements comprises means for making at least five measurements in each set, means for discarding high and low measurements in each set and means for averaging all remaining measured values of the multiple sets.

109. The apparatus according to claim 81, wherein said computational device comprises means for comparing the values of said at least one color factor measured at said first and said further point in time with a stored range of values of said at least one color factor that are found in the colorations of test subjects other than said test subject, to determine where within said range the measured values of said at least one color factor lie.

110. In an apparatus for detecting the condition of a test subject, which condition includes a symptomatic, detectable change in said test subject's coloration; the improvement being characterized by storage means comprising:
   (a) means for compiling a group of lightness measure color factor value ranges, and
   (b) means for associating with each lightness measure color factor value range a value of a color factor for use in comparison with a measurement of the value of that color factor in the coloration of a test subject having a lightness measure color factor value within said range.

111. The apparatus according to claim 110, wherein said instrument includes means for measuring the value of a color factor which is color factor Hunter b or a color factor which is substantially that of color factor Hunter b and said lightness measure color factor value ranges are ranges of values of a color factor which is color factor Hunter L or a color factor which is substantially that of color factor Hunter L, and said apparatus further comprises means for measuring a value of said color factor which is color factor Hunter L or a color factor which is substantially that of color factor Hunter L of said subject's coloration.

112. The apparatus according to claim 81 or 110, wherein said apparatus includes means for detecting a condition that causes jaundice in a human child or adult test subject.

113. The apparatus according to claim 81 or 110, wherein said coloration is skin coloration and said condition is hyperbilirubinemia.

114. The apparatus according to claim 81 or 110, wherein said apparatus includes means for detecting a condition in a biological test subject.

115. The apparatus according to claim 114, wherein said apparatus includes means for detecting a condition in a biological test subject that is selected from the group consisting of plants and soil.

116. The apparatus according to claim 114, wherein said apparatus includes means for detecting a condition in a biological test subject that is selected from the group consisting of tissue, excretions, body fluids, hair and teeth.

117. The apparatus according to claim 81 or 110, wherein said apparatus includes means for detecting a condition in a test subject that is a human infant.

118. The apparatus according to claim 81 or 110, wherein said apparatus includes means for detecting a condition selected from the group consisting of liver disorders, hypertension and tuberculosis.

119. The apparatus according to claim 110, wherein:
   said group of lightness measure value ranges are compiled in machine-readable, tangible form; and
   said associating means associates the color factor value with each lightness measure value range in said machine-readable, tangible form.

120. The apparatus according to claim 119, wherein said color factor value associated with each lightness measure color factor value range is a value of color factor Hunter b or a color factor which is substantially that of color factor Hunter b.

121. The apparatus accordig to claim 120, wherein said lightness measure color factor value is a value of color factor Hunter L or a color factor which is substantially that of color factor Hunter L.

122. The apparatus according to claim 110, wherein:
   the group of lightness measure color factor value ranges compiled are substantially those of color factor Hunter L or a color factor which is substantially that of color factor Hunter L; and
   said associating means associates a value of at least one further color factor whose value is the value of color factor Hunter a or a color factor which is substantially that of color factor Hunter a with each lightness measure color factor value range, the relationship between said lightness measure color factor value ranges and said associated color factor values being substantially as follows:

| Hunter L | Hunter a |
|---|---|
| 24 (or less) to 44 | 4 to 16 |
| 45 to 54 | 4 to 18 |
| 55 to 59 | 5 to 25 |
| 60 to 71 (or more) | 6 to 30 |

123. The apparatus according to claim 110, wherein said associating means associates with each lightness measure value range a value of a yellowness-dependent color factor.

124. The apparatus according to claim 110, wherein the color factor value is of color factor Hunter b or a color factor which is substantially that of color factor Hunter b and the lightness measure value ranges are ranges of color factor Hunter L or a color factor which is substantially that of color factor Hunter L, and the apparatus further comprises an instrument for measuring a value of color factors Hunter L or a value of a color factor which is substantially that of color factor Hunter L of the test subject's coloration.

125. The apparatus according to claim 45 or 110, wherein said ranges of values are determined by ranges of Hunter L values; said ranges of Hunter L values being bounded by at least one of the Hunter L values substantially as follows:
   Hunter L=27, 30, 33, 36, 39, 42, 45, 48, 51, 54, 57, 60, 63, 66 and 69.

126. An apparatus for detecting a condition in a test subject, which condition includes a symptomatic, detectable change in the test subject's coloration, the apparatus comprising:
   (a) a color measuring instrument for measuring at a first point in time and at least at one further point in time a value of at least one color factor in the test subject's coloration, said color factor being dependent, at least in part, on relative content of opponent colors in said coloration and on lightness of said coloration;
   (b) means for storing the measured value of the at least one color factor at said first point in time; and
   (c) means for comparing the measured values of said at least one color factor measured at said first and said at least one further point in time to determine whether there has been exhibited a change therein of a predetermined magnitude evidencing said condition.

127. An apparatus for detecting a condition in a test subject, which condition includes a symptomatic, detectable change in the test subject's coloration, the apparatus comprising:

(a) a color measuring instrument for measuring at a first point in time and at least at one further point in time a value of at least one color factor in the test subject's coloration, said color factor being a factor that comprises a first function weighted in a first portion of the spectrum, a second function weighted in a second portion of the spectrum, and a weighting term that is a function of lightness of said coloration and that modifies the value of the color factor;

(b) means for storing the measured value of the at least one color factor at said first point in time; and (c) means for comparing the measured values of said at least one color factor measured at said first and said at least one further point in time to determine whether there has been exhibited a change therein of a predetermined magnitude evidencing said condition.

128. An apparatus for detecting a condition in a test subject, which condition includes a symptomatic, detectable change in the coloration of the test subject; the apparatus comprising the steps of:

(a) a color measuring instrument for measuring at a first point in time and at further points in time a value of relative content of opponent colors in the coloration of the test subject, (b) means for storing said measured value at said first point in time; and (c) means for comparing the values measured at said first and said further points in time to determine whether there has been exhibited a change therein of a predetermined magnitude that evidences said condition and that is correlatable, in test subjects having colorations of substantially varying degrees of lightness or darkness, to a measure of said condition that has clinical utility.

129. The apparatus according to claim 128, wherein said value of relative content of opponent colors is a value of a color factor that is dependent on lightness of the coloration of the test subject and that modifies the value of the relative content of the opponent colors in said coloration.

130. An apparatus for detecting a condition in a test subject, which condition includes a symptomatic, detectable change in the test subject's coloration; the apparatus comprising:

(a) a color measuring instrument for measuring at a first point in time and at least at one further point in time a value of at least one color factor in the test subject's coloration, said color factor being dependent, at least in part, on relative content of one or more colors in said coloration;

(b) means for storing said measured value at said first point in time;

(c) means for comparing the values of said color factor measured at said first point in time and said at least one further point in time to arrive at a value of change in color factor; and (d) means for comparing the value of change in color factor with a preestablished measure of color factor value change that is known to evidence said condition and that is correlatable, in test subjects having colorations of substantially varying degrees of lightness or darkness, to a measure of the condition that has clinical utility.

131. An apparatus for detecting a condition in a test subject, which condition includes a symptomatic, detectable change in the test subject's coloration; the apparatus comprising:

(a) a color measuring instrument for measuring at a first point in time and at least at one further point in time a value of at least one color factor which is color factor Hunter b or a color factor which is substantially that of color factor Hunter b in the test subject's coloration, said color factor being dependent, at least in part, on relative content of one or more colors in said coloration;

(b) means for storing said measured value of said color factor at said first point in time; and (c) means for comparing the values of said color factor measured at said first point in time and said at least one further point in time to determine whether there has been exhibited a change therein of a predetermined magnitude evidencing said condition.

132. An apparatus for detecting the jaundice caused by hyperbilirubinemia in an infant test subject, which jaundice includes a symptomatic, detectable change in the infant's coloration, the apparatus comprising:

(a) a color measuring instrument for measuring a value of at least one color factor in the infant's coloration at a first point in time following birth when jaundice resulting from hyperbilirubinemia is generally not present in an infant and at least at one further point of time, said color factor being dependent, at least in part, on relative content of one or more colors in said coloration;

(b) means for storing said measured color factor value at said first point in time as a baseline measurement for said infant; and (c) means for comparing the value of said color factor baseline measurement at said first point in time and the value of said color factor measured at said at least one further point in time to determine whether there has been exhibited a change therein of a predetermined magnitude for that particular infant.

133. The apparatus according to either claim 87 or 132, wherein said measured value of at least one color factor measured at a first point in time comprises a value of said color factor measured within two to five hours of the infant's birth.

134. An apparatus for detecting a condition in a test subject, which condition includes a symptomatic, detectable change in the test subject's coloration; the apparatus comprising:

(a) means for storing a plurality of coloration classes in which a predetermined magnitude of a change in value of at least one color factor is indicative of the condition, said predetermined magnitude indicative of the condition differing from one coloration class to another;

(b) a color measuring instrument for measuring at a first point in time and at least at one further point in time a value of the at least one color factor in the test subject's coloration, said color factor being dependent, at least in part, on relative content of one or more colors in said coloration;

(c) means for storing said measured value of said color factor at said first point of time; and (d) means for comparing the values of said color factor measured at said first point in time and said at least one further point in time to determine whether there has been exhibited a change therein of the predetermined magnitude evidencing said condition for the particular coloration class of the test subject.

135. The apparatus according to claim 134, wherein said plurality of coloration classes comprises a plurality of coloration classes that are colorations within varying ranges of lightness.

136. The apparatus according to claim 135, wherein said at least one color factor is color factor Hunter b or a color factor which is substantially that of color factor Hunter b and the coloration classes are defined by ranges of values of color factor Hunter L or a color factor which is substantially that of color factor Hunter L.

137. The apparatus according to claim 136, wherein:

the coloration is skin coloration;

the plurality of coloration classes comprises coloration classes that include a first class of skin coloration having a value of color factor Hunter L or a value of a color factor which is substantially that of color factor Hunter L at or below substantially 51 and a second class of skin coloration having a value of color factor Hunter L or a value of a color factor which is substantially that of color factor Hunter L above substantially 51;

increases in the values of color factor Hunter b or a color factor which is substantially that of color factor Hunter b of substantially two or more points for skin coloration of the first class are indicative of hyperbilirubinemia; and increases in the values of color factor Hunter b or a color factor which is substantially that of color factor Hunter b of substantially three or more points for skin coloration of the second class are indicative of hyperbilirubinemia.

138. The apparatus according to claim 136 or 137, wherein said coloration classes are substantially as follows:

| No. | Hunter L | Hunter b |
|---|---|---|
| 1. | <27 | −5* |
| 2. | <27 | 6 |
| 3. | <27 | 7 |
| 4. | <27 | 8 |
| 5. | <27 | 9 |
| 6. | <27 | 10 |
| 7. | <27 | 11 |
| 8. | <27 | 12+** |
| 9. | 27 to <30 | −5 |
| 10. | 27 to <30 | 6 |
| 11. | 27 to <30 | 7 |
| 12. | 27 to <30 | 8 |
| 13. | 27 to <30 | 9 |
| 14. | 27 to <30 | 10 |
| 15. | 27 to <30 | 11 |
| 16. | 27 to <30 | 12+ |
| 17. | 30 to <33 | −5 |
| 18. | 30 to <33 | 6 |
| 19. | 30 to <33 | 7 |
| 20. | 30 to <33 | 8 |
| 21. | 30 to <33 | 9 |
| 22. | 30 to <33 | 10 |
| 23. | 30 to <33 | 11 |
| 24. | 30 to <33 | 12+ |
| 25. | 33 to <36 | −5 |
| 26. | 33 to <36 | 6 |
| 27. | 33 to <36 | 7 |
| 28. | 33 to <36 | 8 |
| 29. | 33 to <36 | 9 |

-continued

| No. | Hunter L | Hunter b |
|---|---|---|
| 30. | 33 to <36 | 10 |
| 31. | 33 to <36 | 11 |
| 32. | 33 to <36 | 12+ |
| 33. | 36 to <39 | −5 |
| 34. | 36 to <39 | 6 |
| 35. | 36 to <39 | 7 |
| 36. | 36 to <39 | 8 |
| 37. | 36 to <39 | 9 |
| 38. | 36 to <39 | 10 |
| 39. | 36 to <39 | 11 |
| 40. | 36 to <39 | 12 |
| 41. | 36 to <39 | 13 |
| 42. | 36 to <39 | 14 |
| 43. | 36 to <39 | 15+ |
| 44. | 39 to <42 | −5 |
| 45. | 39 to <42 | 6 |
| 46. | 39 to <42 | 7 |
| 47. | 39 to <42 | 8 |
| 48. | 39 to <42 | 9 |
| 49. | 39 to <42 | 10 |
| 50. | 39 to <42 | 11 |
| 51. | 39 to <42 | 12 |
| 52. | 39 to <42 | 13 |
| 53. | 39 to <42 | 14 |
| 54. | 39 to <42 | 15+ |
| 55. | 42 to <45 | −5 |
| 56. | 42 to <45 | 6 |
| 57. | 42 to <45 | 7 |
| 58. | 42 to <45 | 8 |
| 59. | 42 to <45 | 9 |
| 60. | 42 to <45 | 10 |
| 61. | 42 to <45 | 11 |
| 62. | 42 to <45 | 12 |
| 63. | 42 to <45 | 13 |
| 64. | 42 to <45 | 14 |
| 65. | 42 to <45 | 15 |
| 66. | 42 to <45 | 16 |
| 67. | 42 to <45 | 17 |
| 68. | 42 to <45 | 18+ |
| 69. | 45 to <48 | −5 |
| 70. | 45 to <48 | 6 |
| 71. | 45 to <48 | 7 |
| 72. | 45 to <48 | 8 |
| 73. | 45 to <48 | 9 |
| 74. | 45 to <48 | 10 |
| 75. | 45 to <48 | 11 |
| 76. | 45 to <48 | 12 |
| 77. | 45 to <48 | 13 |
| 78. | 45 to <48 | 14 |
| 79. | 45 to <48 | 15 |
| 80. | 45 to <48 | 16 |
| 81. | 45 to <48 | 17 |
| 82. | 45 to <48 | 18+ |
| 83. | 48 to <51 | −5 |
| 84. | 48 to <51 | 6 |
| 85. | 48 to <51 | 7 |
| 86. | 48 to <51 | 8 |
| 87. | 48 to <51 | 9 |
| 88. | 48 to <51 | 10 |
| 89. | 48 to <51 | 11 |
| 90. | 48 to <51 | 12 |
| 91. | 48 to <51 | 13 |
| 92. | 48 to <51 | 14 |
| 93. | 48 to <51 | 15 |
| 94. | 48 to <51 | 16 |
| 95. | 48 to <51 | 17 |
| 96. | 48 to <51 | 18 |
| 97. | 48 to <51 | 19 |
| 98. | 48 to <51 | 20+ |
| 99. | 51 to <54 | −5 |
| 100. | 51 to <54 | 6 |
| 101. | 51 to <54 | 7 |
| 102. | 51 to <54 | 8 |
| 103. | 51 to <54 | 9 |
| 104. | 51 to <54 | 10 |
| 105. | 51 to <54 | 11 |
| 106. | 51 to <54 | 12 |

-continued

| No. | Hunter L | Hunter b |
|---|---|---|
| 107. | 51 to <54 | 13 |
| 108. | 51 to <54 | 14 |
| 109. | 51 to <54 | 15 |
| 110. | 51 to <54 | 16 |
| 111. | 51 to <54 | 17 |
| 112. | 51 to <54 | 18 |
| 113. | 51 to <54 | 19 |
| 114. | 51 to <54 | 20+ |
| 115. | 54 to <57 | −5 |
| 116. | 54 to <57 | 6 |
| 117. | 54 to <57 | 7 |
| 118. | 54 to <57 | 8 |
| 119. | 54 to <57 | 9 |
| 120. | 54 to <57 | 10 |
| 121. | 54 to <57 | 11 |
| 122. | 54 to <57 | 12 |
| 123. | 54 to <57 | 13 |
| 124. | 54 to <57 | 14 |
| 125. | 54 to <57 | 15 |
| 126. | 54 to <57 | 16 |
| 127. | 54 to <57 | 17 |
| 128. | 54 to <57 | 18 |
| 129. | 54 to <57 | 19 |
| 130. | 54 to <57 | 20+ |
| 131. | 57 to <60 | −5 |
| 132. | 57 to <60 | 6 |
| 133. | 57 to <60 | 7 |
| 134. | 57 to <60 | 8 |
| 135. | 57 to <60 | 9 |
| 136. | 57 to <60 | 10 |
| 137. | 57 to <60 | 11 |
| 138. | 57 to <60 | 12 |
| 139. | 57 to <60 | 13 |
| 140. | 57 to <60 | 14 |
| 141. | 57 to <60 | 15 |
| 142. | 57 to <60 | 16 |
| 143. | 57 to <60 | 17 |
| 144. | 57 to <60 | 18 |
| 145. | 57 to <60 | 19 |
| 146. | 57 to <60 | 20+ |
| 147. | 60 to <63 | −5 |
| 148. | 60 to <63 | 6 |
| 149. | 60 to <63 | 7 |
| 150. | 60 to <63 | 8 |
| 151. | 60 to <63 | 9 |
| 152. | 60 to <63 | 10 |
| 153. | 60 to <63 | 11 |
| 154. | 60 to <63 | 12 |
| 155. | 60 to <63 | 13 |
| 156. | 60 to <63 | 14 |
| 157. | 60 to <63 | 15 |
| 158. | 60 to <63 | 16 |
| 159. | 60 to <63 | 17 |
| 160. | 60 to <63 | 18 |
| 161. | 60 to <63 | 19 |
| 162. | 60 to <63 | 20+ |
| 163. | 63 to <66 | −5 |
| 164. | 63 to <66 | 6 |
| 165. | 63 to <66 | 7 |
| 166. | 63 to <66 | 8 |
| 167. | 63 to <66 | 9 |
| 168. | 63 to <66 | 10 |
| 169. | 63 to <66 | 11 |
| 170. | 63 to <66 | 12 |
| 171. | 63 to <66 | 13 |
| 172. | 63 to <66 | 14 |
| 173. | 63 to <66 | 15 |
| 174. | 63 to <66 | 16 |
| 175. | 63 to <66 | 17 |
| 176. | 63 to <66 | 18 |
| 177. | 63 to <66 | 19 |
| 178. | 63 to <66 | 20+ |
| 179. | 66 to <69 | −5 |
| 180. | 66 to <69 | 6 |
| 181. | 66 to <69 | 7 |
| 182. | 66 to <69 | 8 |
| 183. | 66 to <69 | 9 |
| 184. | 66 to <69 | 10 |
| 185. | 66 to <69 | 11 |
| 186. | 66 to <69 | 12 |
| 187. | 66 to <69 | 13 |
| 188. | 66 to <69 | 14 |
| 189. | 66 to <69 | 15 |
| 190. | 66 to <69 | 16 |
| 191. | 66 to <69 | 17 |
| 192. | 66 to <69 | 18 |
| 193. | 66 to <69 | 19 |
| 194. | 66 to <69 | 20+ |
| 195. | ≧69 | −5 |
| 196. | ≧69 | 6 |
| 197. | ≧69 | 7 |
| 198. | ≧69 | 8 |
| 199. | ≧69 | 9 |
| 200. | ≧69 | 10 |
| 201. | ≧69 | 11 |
| 202. | ≧69 | 12 |
| 203. | ≧69 | 13 |
| 204. | ≧69 | 14 |
| 205. | ≧69 | 15 |
| 206. | ≧69 | 16 |
| 207. | ≧69 | 17 |
| 208. | ≧69 | 18 |
| 209. | ≧69 | 19 |
| 210. | ≧69 | 20+ |

Wherein the designation −5 means less than 5 but more than 4 and the designation +12 means more than 12 but less than 13.

139. The apparatus according to claim 134 or 135, wherein said coloration classes are determined by ranges of Hunter L values; said ranges of Hunter L values being bounded by at least one of the Hunter L values substantially as follows:

Hunter L=27, 30, 33, 36, 39, 42, 45, 48, 51, 54, 57, 60, 63, 66 and 69.

140. An apparatus for detecting a medical condition, which condition includes a symptomatic, detectable change in a test subject's coloration; the apparatus comprising:
(a) a color measuring instrument for measuring a value of at least one color factor in the test subject's coloration at a first point in time when the symptomatic, detectable change in coloration resulting from the medical condition is generally not present in a test subject and at least one further point in time, said color factor being dependent, at least in part, on relative content of one or more colors in said coloration;
(b) means for storing said measured color factor value at said first point in time as a baseline measurement for said test subject; and
(c) means for comparing the value of said color factor baseline measurement at said first point in time and the value of said color factor measured at said at least one further point in time to determine whether there has been exhibited a change therein of a predetermined magnitude for that particular test subject.

141. The apparatus according to any one of claims 126, 127, 132, 140, wherein said at least one color factor comprises a first function weighted in a yellower portion of the spectrum and a second function weighed in a bluer portion of the spectrum.

142. The apparatus according to claim 126 or 140, wherein said at least one color factor is color factor Hunter a or a color factor which is substantially that of color factor Hunter a.

143. The apparatus according to any one of claims 130, 132 or 140, wherein said color factor is further dependent on lightness of the coloration of the test subject.

144. An apparatus for detecting a condition in a test subject, which condition includes a symptomatic, detectable change in the test subject's coloration, the apparatus comprising:
- (a) a color measuring instrument for measuring at a first point in time and at least at one further point in time a value of at least one color factor in the test subject's coloration, said color factor being dependent, at least in part, on relative content of one or more colors in said coloration and on the lightness of said coloration; and
- (b) means for comparing the values of said color factor in the test subject's coloration measured at said first point in time and said at least at one further point in time to determine whether there has been established a change therein of a predetermined magnitude evidencing said condition.

145. The apparatus according to any one of claims 126, 127, 130, 131, 132, 134, 140 or 144, wherein said color measuring instrument includes means for averaging a set of multiple measurements of the color factor value.

146. The apparatus according to any one of claims 126, 127, 130, 131, 132, 134, 140 or 144, wherein said color measuring instrument includes means for measuring the value of said factor at different locations on the test subject.

147. The apparatus according to any one of claims 126, 127, 130, 132, 134, 140 or 144, wherein said color factor is dependent on the relative content of opponent colors in said coloration.

148. The apparatus according to any one of claims 126, 127, 128, 130, 131, 132, 140 or 144, further comprising means for storing a plurality of previously established coloration classes in each of which a preestablished magnitude of change in value of said color factor is indicative of said condition.

149. The apparatus according to any one of claims 126, 127, 128, 130, 132, 134, 140 or 144, wherein said color factor is dependent on relative content of blue and yellow in said coloration.

150. The apparatus according to any one of claims 126, 127, 128, 130, 132, 134, 140 or 144, wherein said color factor is dependent on relative content of green and red in said coloration.

151. The apparatus according to any one of claims 126, 127, 128, 130, 132, 134, 140, or 144, wherein said color factor is dependent on yellowness of the coloration of the test subject.

152. The apparatus according to any one of claims 126, 127, 128, 130, 132, 134, 140 and 144, wherein said color factor is color factor Hunter b or a color factor which is substantially that of color factor Hunter b.

153. The apparatus according to any one of claims 126, 127, 130, 132, 134, 140 or 144, wherein said color factor comprises a first function weighted in a first portion of the spectrum and a second function weighted in a second portion of the spectrum, the color factor being further dependent on lightness of the coloration of the test subject.

154. The apparatus of claim 144, wherein:
said at least one color factor value is color factor Hunter b or a color factor which is substantially that of color factor Hunter b;
said color measuring instrument includes means for measuring a value of color factor Hunter a or a color factor which is substantially that of color factor Hunter a; and
said comparing means includes means for comparing a measured value of color factor Hunter a or a color factor which is substantially that of color factor Hunter a with a range of values of color factor Hunter a or a color factor which is substantially that of color factor Hunter a to determine whether the measured value of color factor Hunter a or a color factor which is substantially that of color factor Hunter a lies within an acceptable range.

155. The apparatus according to claim 144, further comprising means for storing a previously established range of values of the color factor characteristic of subjects without said condition.

156. The apparatus according to any one of claims 110, 126, 127, 128, 130, 131, 134, 140, or 144, wherein said condition to be detected is a condition that causes jaundice in a human child or adult test subject.

157. The apparatus according to any one of claims 110, 126, 127, 128, 130, 131, 134, 140, or 144, wherein the coloration is skin coloration, and the condition to be detected is hyperbilirubinemia.

158. The apparatus according to any one of claims 110, 126, 127, 128, 130, 131, 134, 140, or 144, wherein the test subject is a biological test subject.

159. The apparatus according to claim 158, wherein the biological test subject is a human or animal test subject.

160. The apparatus according to claim 159, wherein the test subject is a human infant.

161. The apparatus according to claim 158, wherein the biological test subject is selected from the group consisting of plants and soil.

162. The apparatus according to claim 158, wherein the biological test subject is selected from the group consisting of tissue, excretions, body fluids, hair and teeth.

163. The apparatus according to any one of claims 110, 126, 127, 128, 130, 131, 134, 140 or 144, wherein said condition is selected from the group consisting of liver disorders, hypertension, and tuberculosis.

164. The apparatus according to any one of claims 81, 110, 126, 130, 131, 132, 134, 140 or 144, further comprising means for comparing measurements of a further color factor value at first and further points in time and means for discontinuing the detection procedure of the apparatus in response to a change in the further color factor value greater than a predetermined amount.

165. The apparatus according to claim 164, wherein the further color factor is color factor Hunter a or a color factor which is substantially that of color factor Hunter a.

166. The apparatus according to claim 164, wherein the further color factor is color factor Hunter L or a color factor which is substantially that of color factor Hunter L.

167. The apparatus according to claim 166, wherein the predetermined amount of change is an amount substantially that of a change in value of color factor Hunter L or a color factor which is substantially that of color factor Hunter L of 3 to 5 points.

168. An apparatus for detecting hyperbilirubinemia in a test subject based on skin coloration of said test subject, comprising:
- (a) a color measuring instrument for measuring a value of a first color factor, whose value is substantially that of Hunter b in said skin coloration of the test subject, and a value of a second color factor, whose value is substantially that of Hunter L in said skin coloration of the test subject; and
- (b) means for comparing the measured value of said first color factor with a range of acceptable values of said first color factor that are found in subjects in the absence of hyperbilirubinemia, said subjects having a skin coloration corresponding to the particular measured value of said second color factor in said test subject to determine if the measured value of said first color factor lies inside or outside the range, wherein said range of acceptable values is selected from ranges substantially as follows:

| No. | Hunter L | Hunter b |
|---|---|---|
| 1. | <27 | −5* |
| 2. | <27 | 6 |
| 3. | <27 | 7 |
| 4. | <27 | 8 |
| 5. | <27 | 9 |
| 6. | <27 | 10 |
| 7. | <27 | 11 |
| 8. | <27 | 12+** |
| 9. | 27 to −30 | −5 |
| 10. | 27 to −30 | 6 |
| 11. | 27 to −30 | 7 |
| 12. | 27 to −30 | 8 |
| 13. | 27 to −30 | 9 |
| 14. | 27 to −30 | 10 |
| 15. | 27 to −30 | 11 |
| 16. | 27 to −30 | 12+ |
| 17. | 30 to <33 | −5 |
| 18. | 30 to <33 | 6 |
| 19. | 30 to <33 | 7 |
| 20. | 30 to <33 | 8 |
| 21. | 30 to <33 | 9 |
| 22. | 30 to <33 | 10 |
| 23. | 30 to <33 | 11 |
| 24. | 30 to <33 | 12+ |
| 25. | 33 to <36 | −5 |
| 26. | 33 to <36 | 6 |
| 27. | 33 to <36 | 7 |
| 28. | 33 to <36 | 8 |
| 29. | 33 to <36 | 9 |
| 30. | 33 to <36 | 10 |
| 31. | 33 to <36 | 11 |
| 32. | 33 to <36 | 12+ |
| 33. | 36 to <39 | −5 |
| 34. | 36 to <39 | 6 |
| 35. | 36 to <39 | 7 |
| 36. | 36 to <39 | 8 |
| 37. | 36 to <39 | 9 |
| 38. | 36 to <39 | 10 |
| 39. | 36 to <39 | 11 |
| 40. | 36 to <39 | 12 |
| 41. | 36 to <39 | 13 |
| 42. | 36 to <39 | 14 |
| 43. | 36 to <39 | 15+ |
| 44. | 39 to <42 | −5 |
| 45. | 39 to <42 | 6 |
| 46. | 39 to <42 | 7 |
| 47. | 39 to <42 | 8 |
| 48. | 39 to <42 | 9 |
| 49. | 39 to <42 | 10 |
| 50. | 39 to <42 | 11 |
| 51. | 39 to <42 | 12 |
| 52. | 39 to <42 | 13 |
| 53. | 39 to <42 | 14 |
| 54. | 39 to <42 | 15+ |
| 55. | 42 to <45 | −5 |
| 56. | 42 to <45 | 6 |
| 57. | 42 to <45 | 7 |
| 58. | 42 to <45 | 8 |
| 59. | 42 to <45 | 9 |
| 60. | 42 to <45 | 10 |
| 61. | 42 to <45 | 11 |
| 62. | 42 to <45 | 12 |
| 63. | 42 to <45 | 13 |
| 64. | 42 to <45 | 14 |
| 65. | 42 to <45 | 15 |
| 66. | 42 to <45 | 16 |
| 67. | 42 to <45 | 17 |
| 68. | 42 to <45 | 18+ |
| 69. | 45 to <48 | −5 |
| 70. | 45 to <48 | 6 |

-continued

| No. | Hunter L | Hunter b |
|---|---|---|
| 71. | 45 to <48 | 7 |
| 72. | 45 to <48 | 8 |
| 73. | 45 to <48 | 9 |
| 74. | 45 to <48 | 10 |
| 75. | 45 to <48 | 11 |
| 76. | 45 to <48 | 12 |
| 77. | 45 to <48 | 13 |
| 78. | 45 to <48 | 14 |
| 79. | 45 to <48 | 15 |
| 80. | 45 to <48 | 16 |
| 81. | 45 to <48 | 17 |
| 82. | 45 to <48 | 18+ |
| 83. | 48 to <51 | −5 |
| 84. | 48 to <51 | 6 |
| 85. | 48 to <51 | 7 |
| 86. | 48 to <51 | 8 |
| 87. | 48 to <51 | 9 |
| 88. | 48 to <51 | 10 |
| 89. | 48 to <51 | 11 |
| 90. | 48 to <51 | 12 |
| 91. | 48 to <51 | 13 |
| 92. | 48 to <51 | 14 |
| 93. | 48 to <51 | 15 |
| 94. | 48 to <51 | 16 |
| 95. | 48 to <51 | 17 |
| 96. | 48 to <51 | 18 |
| 97. | 48 to <51 | 19 |
| 98. | 48 to <51 | 20+ |
| 99. | 51 to <54 | −5 |
| 100. | 51 to <54 | 6 |
| 101. | 51 to <54 | 7 |
| 102. | 51 to <54 | 8 |
| 103. | 51 to <54 | 9 |
| 104. | 51 to <54 | 10 |
| 105. | 51 to <54 | 11 |
| 106. | 51 to <54 | 12 |
| 107. | 51 to <54 | 13 |
| 108. | 51 to <54 | 14 |
| 109. | 51 to <54 | 15 |
| 110. | 51 to <54 | 16 |
| 111. | 51 to <54 | 17 |
| 112. | 51 to <54 | 18 |
| 113. | 51 to <54 | 19 |
| 114. | 51 to <54 | 20+ |
| 115. | 54 to <57 | −5 |
| 116. | 54 to <57 | 6 |
| 117. | 54 to <57 | 7 |
| 118. | 54 to <57 | 8 |
| 119. | 54 to <57 | 9 |
| 120. | 54 to <57 | 10 |
| 121. | 54 to <57 | 11 |
| 122. | 54 to <57 | 12 |
| 123. | 54 to <57 | 13 |
| 124. | 54 to <57 | 14 |
| 125. | 54 to <57 | 15 |
| 126. | 54 to <57 | 16 |
| 127. | 54 to <57 | 17 |
| 128. | 54 to <57 | 18 |
| 129. | 54 to <57 | 19 |
| 130. | 54 to <57 | 20+ |
| 131. | 57 to <60 | −5 |
| 132. | 57 to <60 | 6 |
| 133. | 57 to <60 | 7 |
| 134. | 57 to <60 | 8 |
| 135. | 57 to <60 | 9 |
| 136. | 57 to <60 | 10 |
| 137. | 57 to <60 | 11 |
| 138. | 57 to <60 | 12 |
| 139. | 57 to <60 | 13 |
| 140. | 57 to <60 | 14 |
| 141. | 57 to <60 | 15 |
| 142. | 57 to <60 | 16 |
| 143. | 57 to <60 | 17 |
| 144. | 57 to <60 | 18 |
| 145. | 57 to <60 | 19 |
| 146. | 57 to <60 | 20+ |
| 147. | 60 to <63 | −5 |

-continued

| No. | Hunter L | Hunter b |
|---|---|---|
| 148. | 60 to <63 | 6 |
| 149. | 60 to <63 | 7 |
| 150. | 60 to <63 | 8 |
| 151. | 60 to <63 | 9 |
| 152. | 60 to <63 | 10 |
| 153. | 60 to <63 | 11 |
| 154. | 60 to <63 | 12 |
| 155. | 60 to <63 | 13 |
| 156. | 60 to <63 | 14 |
| 157. | 60 to <63 | 15 |
| 158. | 60 to <63 | 16 |
| 159. | 60 to <63 | 17 |
| 160. | 60 to <63 | 18 |
| 161. | 60 to <63 | 19 |
| 162. | 60 to <63 | 20+ |
| 163. | 63 to <66 | −5 |
| 164. | 63 to <66 | 6 |
| 165. | 63 to <66 | 7 |
| 166. | 63 to <66 | 8 |
| 167. | 63 to <66 | 9 |
| 168. | 63 to <66 | 10 |
| 169. | 63 to <66 | 11 |
| 170. | 63 to <66 | 12 |
| 171. | 63 to <66 | 13 |
| 172. | 63 to <66 | 14 |
| 173. | 63 to <66 | 15 |
| 174. | 63 to <66 | 16 |
| 175. | 63 to <66 | 17 |
| 176. | 63 to <66 | 18 |
| 177. | 63 to <66 | 19 |
| 178. | 63 to <66 | 20+ |
| 179. | 66 to <69 | −5 |
| 180. | 66 to <69 | 6 |
| 181. | 66 to <69 | 7 |
| 182. | 66 to <69 | 8 |
| 183. | 66 to <69 | 9 |
| 184. | 66 to <69 | 10 |
| 185. | 66 to <69 | 11 |
| 186. | 66 to <69 | 12 |
| 187. | 66 to <69 | 13 |
| 188. | 66 to <69 | 14 |
| 189. | 66 to <69 | 15 |
| 190. | 66 to <69 | 16 |
| 191. | 66 to <69 | 17 |
| 192. | 66 to <69 | 18 |
| 193. | 66 to <69 | 19 |
| 194. | 66 to <69 | 20+ |
| 195. | ≧69 | −5 |
| 196. | ≧69 | 6 |
| 197. | ≧69 | 7 |
| 198. | ≧69 | 8 |
| 199. | ≧69 | 9 |
| 200. | ≧69 | 10 |
| 201. | ≧69 | 11 |
| 202. | ≧69 | 12 |
| 203. | ≧69 | 13 |
| 204. | ≧69 | 14 |
| 205. | ≧69 | 15 |
| 206. | ≧69 | 16 |
| 207. | ≧69 | 17 |
| 208. | ≧69 | 18 |
| 209. | ≧69 | 19 |
| 210. | ≧69 | 20+ |

Wherein the designation −5 means less than 5 but more than 4 and the designation +12 means more than 12 but less than 13.

169. In an apparatus for determining a color characteristic, the improvement comprising:
 (a) means for compiling a group of lightness measure color factor value ranges, said lightness measure color factor comprising a color factor whose value is substantially that of color factor Hunter L, and
 (b) means for associating with each lightness measure color factor value range a value of at least one further color factor for use in comparison with a measurement of the value of that color factor in the coloration of a test subject having a lightness measure color factor value in said range, said at least one further color factor comprising a color factor whose value is substantially that of color factor Hunter b and the relationship between said lightness measure color factor value ranges and said associated color factor values being substantially as follows:

| No. | Hunter L | Hunter b |
|---|---|---|
| 1. | <27 | −5* |
| 2. | <27 | 6 |
| 3. | <27 | 7 |
| 4. | <27 | 8 |
| 5. | <27 | 9 |
| 6. | <27 | 10 |
| 7. | <27 | 11 |
| 8. | <27 | 12+** |
| 9. | 27 to −30 | −5 |
| 10. | 27 to −30 | 6 |
| 11. | 27 to −30 | 7 |
| 12. | 27 to −30 | 8 |
| 13. | 27 to −30 | 9 |
| 14. | 27 to −30 | 10 |
| 15. | 27 to −30 | 11 |
| 16. | 27 to −30 | 12+ |
| 17. | 30 to <33 | −5 |
| 18. | 30 to <33 | 6 |
| 19. | 30 to <33 | 7 |
| 20. | 30 to <33 | 8 |
| 21. | 30 to <33 | 9 |
| 22. | 30 to <33 | 10 |
| 23. | 30 to <33 | 11 |
| 24. | 30 to <33 | 12+ |
| 25. | 33 to <36 | −5 |
| 26. | 33 to <36 | 6 |
| 27. | 33 to <36 | 7 |
| 28. | 33 to <36 | 8 |
| 29. | 33 to <36 | 9 |
| 30. | 33 to <36 | 10 |
| 31. | 33 to <36 | 11 |
| 32. | 33 to <36 | 12+ |
| 33. | 36 to <39 | −5 |
| 34. | 36 to <39 | 6 |
| 35. | 36 to <39 | 7 |
| 36. | 36 to <39 | 8 |
| 37. | 36 to <39 | 9 |
| 38. | 36 to <39 | 10 |
| 39. | 36 to <39 | 11 |
| 40. | 36 to <39 | 12 |
| 41. | 36 to <39 | 13 |
| 42. | 36 to <39 | 14 |
| 43. | 36 to <39 | 15+ |
| 44. | 39 to <42 | −5 |
| 45. | 39 to <42 | 6 |
| 46. | 39 to <42 | 7 |
| 47. | 39 to <42 | 8 |
| 48. | 39 to <42 | 9 |
| 49. | 39 to <42 | 10 |
| 50. | 39 to <42 | 11 |
| 51. | 39 to <42 | 12 |
| 52. | 39 to <42 | 13 |
| 53. | 39 to <42 | 14 |
| 54. | 39 to <42 | 15+ |
| 55. | 42 to <45 | −5 |
| 56. | 42 to <45 | 6 |
| 57. | 42 to <45 | 7 |
| 58. | 42 to <45 | 8 |
| 59. | 42 to <45 | 9 |
| 60. | 42 to <45 | 10 |
| 61. | 42 to <45 | 11 |
| 62. | 42 to <45 | 12 |
| 63. | 42 to <45 | 13 |
| 64. | 42 to <45 | 14 |
| 65. | 42 to <45 | 15 |
| 66. | 42 to <45 | 16 |
| 67. | 42 to <45 | 17 |

-continued

| No. | Hunter L | Hunter b |
|---|---|---|
| 68. | 42 to <45 | 18+ |
| 69. | 45 to <48 | −5 |
| 70. | 45 to <48 | 6 |
| 71. | 45 to <48 | 7 |
| 72. | 45 to <48 | 8 |
| 73. | 45 to <48 | 9 |
| 74. | 45 to <48 | 10 |
| 75. | 45 to <48 | 11 |
| 76. | 45 to <48 | 12 |
| 77. | 45 to <48 | 13 |
| 78. | 45 to <48 | 14 |
| 79. | 45 to <48 | 15 |
| 80. | 45 to <48 | 16 |
| 81. | 45 to <48 | 17 |
| 82. | 45 to <48 | 18+ |
| 83. | 48 to <51 | −5 |
| 84. | 48 to <51 | 6 |
| 85. | 48 to <51 | 7 |
| 86. | 48 to <51 | 8 |
| 87. | 48 to <51 | 9 |
| 88. | 48 to <51 | 10 |
| 89. | 48 to <51 | 11 |
| 90. | 48 to <51 | 12 |
| 91. | 48 to <51 | 13 |
| 92. | 48 to <51 | 14 |
| 93. | 48 to <51 | 15 |
| 94. | 48 to <51 | 16 |
| 95. | 48 to <51 | 17 |
| 96. | 48 to <51 | 18 |
| 97. | 48 to <51 | 19 |
| 98. | 48 to <51 | 20+ |
| 99. | 51 to <54 | −5 |
| 100. | 51 to <54 | 6 |
| 101. | 51 to <54 | 7 |
| 102. | 51 to <54 | 8 |
| 103. | 51 to <54 | 9 |
| 104. | 51 to <54 | 10 |
| 105. | 51 to <54 | 11 |
| 106. | 51 to <54 | 12 |
| 107. | 51 to <54 | 13 |
| 108. | 51 to <54 | 14 |
| 109. | 51 to <54 | 15 |
| 110. | 51 to <54 | 16 |
| 111. | 51 to <54 | 17 |
| 112. | 51 to <54 | 18 |
| 113. | 51 to <54 | 19 |
| 114. | 51 to <54 | 20+ |
| 115. | 54 to <57 | −5 |
| 116. | 54 to <57 | 6 |
| 117. | 54 to <57 | 7 |
| 118. | 54 to <57 | 8 |
| 119. | 54 to <57 | 9 |
| 120. | 54 to <57 | 10 |
| 121. | 54 to <57 | 11 |
| 122. | 54 to <57 | 12 |
| 123. | 54 to <57 | 13 |
| 124. | 54 to <57 | 14 |
| 125. | 54 to <57 | 15 |
| 126. | 54 to <57 | 16 |
| 127. | 54 to <57 | 17 |
| 128. | 54 to <57 | 18 |
| 129. | 54 to <57 | 19 |
| 130. | 54 to <57 | 20+ |
| 131. | 57 to <60 | −5 |
| 132. | 57 to <60 | 6 |
| 133. | 57 to <60 | 7 |
| 134. | 57 to <60 | 8 |
| 135. | 57 to <60 | 9 |
| 136. | 57 to <60 | 10 |
| 137. | 57 to <60 | 11 |
| 138. | 57 to <60 | 12 |
| 139. | 57 to <60 | 13 |
| 140. | 57 to <60 | 14 |
| 141. | 57 to <60 | 15 |
| 142. | 57 to <60 | 16 |
| 143. | 57 to <60 | 17 |
| 144. | 57 to <60 | 18 |

-continued

| No. | Hunter L | Hunter b |
|---|---|---|
| 145. | 57 to <60 | 19 |
| 146. | 57 to <60 | 20+ |
| 147. | 60 to <63 | −5 |
| 148. | 60 to <63 | 6 |
| 149. | 60 to <63 | 7 |
| 150. | 60 to <63 | 8 |
| 151. | 60 to <63 | 9 |
| 152. | 60 to <63 | 10 |
| 153. | 60 to <63 | 11 |
| 154. | 60 to <63 | 12 |
| 155. | 60 to <63 | 13 |
| 156. | 60 to <63 | 14 |
| 157. | 60 to <63 | 15 |
| 158. | 60 to <63 | 16 |
| 159. | 60 to <63 | 17 |
| 160. | 60 to <63 | 18 |
| 161. | 60 to <63 | 19 |
| 162. | 60 to <63 | 20+ |
| 163. | 63 to <66 | −5 |
| 164. | 63 to <66 | 6 |
| 165. | 63 to <66 | 7 |
| 166. | 63 to <66 | 8 |
| 167. | 63 to <66 | 9 |
| 168. | 63 to <66 | 10 |
| 169. | 63 to <66 | 11 |
| 170. | 63 to <66 | 12 |
| 171. | 63 to <66 | 13 |
| 172. | 63 to <66 | 14 |
| 173. | 63 to <66 | 15 |
| 174. | 63 to <66 | 16 |
| 175. | 63 to <66 | 17 |
| 176. | 63 to <66 | 18 |
| 177. | 63 to <66 | 19 |
| 178. | 63 to <66 | 20+ |
| 179. | 66 to <69 | −5 |
| 180. | 66 to <69 | 6 |
| 181. | 66 to <69 | 7 |
| 182. | 66 to <69 | 8 |
| 183. | 66 to <69 | 9 |
| 184. | 66 to <69 | 10 |
| 185. | 66 to <69 | 11 |
| 186. | 66 to <69 | 12 |
| 187. | 66 to <69 | 13 |
| 188. | 66 to <69 | 14 |
| 189. | 66 to <69 | 15 |
| 190. | 66 to <69 | 16 |
| 191. | 66 to <69 | 17 |
| 192. | 66 to <69 | 18 |
| 193. | 66 to <69 | 19 |
| 194. | 66 to <69 | 20+ |
| 195. | ≧69 | −5 |
| 196. | ≧69 | 6 |
| 197. | ≧69 | 7 |
| 198. | ≧69 | 8 |
| 199. | ≧69 | 9 |
| 200. | ≧69 | 10 |
| 201. | ≧69 | 11 |
| 202. | ≧69 | 12 |
| 203. | ≧69 | 13 |
| 204. | ≧69 | 14 |
| 205. | ≧69 | 15 |
| 206. | ≧69 | 16 |
| 207. | ≧69 | 17 |
| 208. | ≧69 | 18 |
| 209. | ≧69 | 19 |
| 210. | ≧69 | 20+ |

Wherein the designation −5 means less than 5 but more than 4 and the designation +12 means more than 12 but less than 13.

170. The apparatus according to claim 169, wherein the apparatus for determining a color characteristic comprises means for determining a color characteristic in a biological test subject.

171. The apparatus according to claim 169, wherein the apparatus for determining a color characteristic comprises means for determining a color characteristic in a biological test subject that is a human or animal test subject.

172. In an apparatus for determining a color characteristic, the improvement comprising:
   (a) means for compiling a group of lightness measure color factor value ranges, said ranges comprising at least one range of a color factor whose value is substantially that of color factor Hunter L, said at least one range being selected from the ranges substantially as follows:
   Hunter L=<27, 27 to <30, 30 to <33, 33 to <36, 36 to <39, 39 to <42, 42 to <45, 45 to <48, 48 to <51, 51 to <54, 54 to <57, 57 to <60, 60 to <63, 63 to <66, 66 to <69, and $\leq 69$, and
   (b) means for associating with each lightness measure color factor value range a value of a color factor for use in comparison with a measurement of the value of that color factor in the coloration of a test subject having a lightness measure color factor value within said range.

173. In an apparatus for evaluating the coloration of a test subject, the improvement comprising:
   (a) means for compiling a group of lightness measure color factor value ranges, said lightness measure color factor comprising a color factor whose value is substantially that of color factor Hunter L; and
   (b) means for associating with each lightness measure color factor value range a value of at least one further color factor for use in comparison with a measurement of the value of that color factor in the coloration of a test subject having a lightness measure color value in said range, said at least one further color factor comprising a color factor whose value is substantially that of at least one of color factors Hunter b and Hunter a, and the relationship between said lightness measure color factor value ranges and said associated color factor values being substantially as follows:

| CATEGORY NAME | L Min | L Max | a Min | a Max | b Min | b Max |
|---|---|---|---|---|---|---|
| Black | 0.00 | 14.00 | −10.00 | 3.00 | −10.00 | 5.00 |
| Darkest Dark Brown | 14.00 | 16.00 | −10.00 | 3.00 | −10.00 | 1.00 |
| Darkest Dark Brown | 14.00 | 16.00 | −10.00 | 3.00 | 1.00 | 1.15 |
| Darkest Dark Brown | 14.00 | 16.00 | −10.00 | 3.00 | 1.15 | 1.25 |
| Darkest Dark Brown | 14.00 | 16.00 | −10.00 | 3.00 | 1.25 | 3.00 |
| Darker Dark Brown | 16.00 | 19.00 | −10.00 | 3.00 | −10.00 | 2.70 |
| Darker Dark Brown | 16.00 | 19.00 | −10.00 | 3.00 | 2.70 | 2.95 |
| Darker Dark Brown | 16.00 | 19.00 | −10.00 | 3.00 | 2.95 | 3.20 |
| Darker Dark Brown | 16.00 | 19.00 | −10.00 | 3.00 | 3.20 | 10.00 |
| Darker Dark Brown (Cool Auburn Tones) | 16.00 | 19.00 | 2.00 | 3.00 | −10.00 | 2.70 |
| Darker Dark Brown (Warm Auburn Tones) | 16.00 | 19.00 | 2.00 | 3.00 | 3.20 | 10.00 |
| Brown | 19.00 | 22.00 | 0.00 | 6.00 | −10.00 | 2.95 |
| Brown | 19.00 | 22.00 | 0.00 | 6.00 | 2.95 | 3.20 |
| Brown | 19.00 | 22.00 | 0.00 | 6.00 | 3.20 | 3.45 |
| Brown | 19.00 | 22.00 | 0.00 | 6.00 | 3.45 | 10.00 |
| Brown (Warm Auburn Tones) | 19.00 | 22.00 | 3.50 | 6.00 | 3.45 | 10.00 |
| Brown (Cool Auburn Tones) | 19.00 | 22.00 | 3.50 | 6.00 | −10.00 | 3.45 |
| Medium Brown | 22.00 | 27.00 | 1.00 | 6.00 | −10.00 | 3.75 |
| Medium Brown | 22.00 | 27.00 | 1.00 | 6.00 | 3.75 | 4.00 |
| Golden Med. Brown | 22.00 | 27.00 | 1.00 | 6.00 | 4.00 | 4.25 |
| Golden Med. Brown | 22.00 | 27.00 | 1.00 | 6.00 | 4.25 | 10.00 |
| Medium Brown (Warm Auburn Tones) | 22.00 | 27.00 | 3.50 | 6.00 | 4.25 | 10.00 |
| Medium Brown (Cool Auburn Tones) | 22.00 | 27.00 | 3.50 | 6.00 | −10.00 | 4.25 |
| Darkest Med. Blonde | 27.00 | 28.00 | 1.80 | 6.00 | −5.00 | 6.00 |
| Darkest Med. Blonde | 27.00 | 28.00 | 1.80 | 5.00 | 6.00 | 6.50 |
| Darkest Med. Blonde | 27.00 | 28.00 | 5.00 | 6.00 | 6.00 | 6.50 |
| Darkest Med. Blonde | 27.00 | 28.00 | 1.80 | 6.00 | 6.50 | 15.00 |
| Medium Blonde | 28.00 | 31.00 | 1.80 | 6.00 | −5.00 | 6.00 |
| Medium Blonde | 28.00 | 31.00 | 1.80 | 5.00 | 6.00 | 6.50 |
| Med. Golden Blonde | 28.00 | 31.00 | 5.00 | 6.00 | 6.00 | 6.50 |
| Med. Golden Blonde | 28.00 | 31.00 | 1.80 | 6.00 | 6.50 | 15.00 |
| Lightest Med. Blonde | 31.00 | 33.00 | 1.80 | 6.00 | −5.00 | 6.00 |
| Lightest Med. Blonde | 31.00 | 33.00 | 1.80 | 5.00 | 6.00 | 6.50 |
| Lightest Med. Blonde | 31.00 | 33.00 | 5.00 | 6.00 | 6.00 | 6.50 |
| Lightest Med. Blonde | 31.00 | 33.00 | 1.80 | 6.00 | 6.50 | 15.00 |
| Light Blonde | 33.00 | 36.00 | 1.80 | 6.00 | −5.00 | 7.00 |
| Light Blonde | 33.00 | 36.00 | 1.80 | 5.00 | 7.00 | 7.50 |
| Light Blonde | 33.00 | 36.00 | 5.00 | 6.00 | 7.00 | 7.50 |
| Light Blonde | 33.00 | 36.00 | 1.80 | 6.00 | 7.50 | 20.00 |
| Lighter Blonde | 36.00 | 40.00 | 1.80 | 6.00 | −5.00 | 8.00 |
| Lighter Blonde | 36.00 | 40.00 | 1.80 | 5.00 | 8.00 | 8.50 |
| Lighter Blonde | 36.00 | 40.00 | 5.00 | 6.00 | 8.00 | 8.50 |
| Lighter Blonde | 36.00 | 40.00 | 1.80 | 6.00 | 8.50 | 20.00 |

-continued

| CATEGORY NAME | L Min | L Max | a Min | a Max | b Min | b Max |
|---|---|---|---|---|---|---|
| Lightest Blonde | 40.00 | 80.00 | 1.80 | 7.00 | −5.00 | 9.00 |
| Lightest Blonde | 40.00 | 80.00 | 1.80 | 5.00 | 9.00 | 10.00 |
| Lightest Blonde | 40.00 | 80.00 | 5.00 | 7.00 | 9.00 | 10.00 |
| Lightest Blonde | 40.00 | 80.00 | 1.80 | 7.00 | 10.00 | 30.00 |
| Light Red | 22.00 | 28.00 | 6.00 | 30.00 | 5.00 | 3.50 |
| Light Red | 22.00 | 28.00 | 6.00 | 30.00 | 3.50 | 3.75 |
| Light Red | 22.00 | 28.00 | 6.00 | 30.00 | 3.75 | 4.00 |
| Light Red | 22.00 | 28.00 | 6.00 | 30.00 | 4.00 | 30.00 |
| Medium Red | 19.00 | 22.00 | 6.00 | 30.00 | −10.00 | 3.50 |
| Medium Red | 19.00 | 22.00 | 6.00 | 30.00 | 3.50 | 3.75 |
| Med. Golden Red | 19.00 | 22.00 | 6.00 | 30.00 | 3.75 | 4.00 |
| Med. Golden Red | 19.00 | 22.00 | 6.00 | 30.00 | 4.00 | 30.00 |
| Dark Red | 14.00 | 19.00 | 3.00 | 30.00 | −10.00 | 2.50 |
| Dark Red | 14.00 | 19.00 | 3.00 | 30.00 | 2.50 | 2.75 |
| Dark Red | 14.00 | 19.00 | 3.00 | 30.00 | 2.75 | 3.00 |
| Dark Red | 14.00 | 19.00 | 3.00 | 30.00 | 3.00 | 30.00 |
| Red Blonde | 27.00 | 40.00 | 6.00 | 30.00 | 6.00 | 30.00 |
| Red Blonde | 40.00 | 80.00 | 7.00 | 30.00 | 6.00 | 30.00 |
| Black/Dk Brown/Med Brown/Brown w/ 70%–90% Grey | 27.00 | 50.00 | −10.00 | 1.80 | −10.00 | 3.75 |
| Black/Dk Brown/Med Brown/Brown w/ 70%–90% Grey | 27.00 | 50.00 | −10.00 | 1.80 | 3.75 | 4.00 |
| Black/Dk Brown/Med Brown/Brown w/ 70%–90% Grey | 27.00 | 50.00 | −10.00 | 1.80 | 4.00 | 4.25 |
| Black/Dk Brown/Med Brown/Brown w/ 70%–90% Grey | 27.00 | 50.00 | −10.00 | 1.80 | 4.25 | 10.00 |
| Black/Dk Brown/Med Brown/Brown w/ 40%–60% Grey | 23.00 | 27.00 | −10.00 | 1.00 | −10.00 | 3.75 |
| Black/Dk Brown/Med Brown/Brown w/ 40%–60% Grey | 23.00 | 27.00 | −10.00 | 1.00 | 3.75 | 4.00 |
| Black/Dk Brown/Med Brown/Brown w/ 40%–60% Grey | 23.00 | 27.00 | −10.00 | 1.00 | 4.00 | 4.25 |
| Black/Dk Brown/Med Brown/Brown w/ 40%–60% Grey | 23.00 | 27.00 | −10.00 | 1.00 | 4.25 | 10.00 |
| For Grey Hair | | | | | | |
| Light Brown/Darkest Blonde | | | | | | |
| 40%–60% Grey | 4.00 | 10.00 | −10.00 | −0.08 | | |
| 70%–90% Grey | 10.00 | To Maximum | −10.00 | −0.08 | | |
| Dark Red, Medium Red or Medium Light Red | | | | | | |
| 40%–60% Grey | 6.00 | 10.00 | −10.00 | −0.80 | | |
| 70%–90% Grey | 10.00 | To Maximum | −10.00 | −0.80 | | |
| Light Red or Red Blonde | | | | | | |
| 40%–60% Grey | 5.00 | 7.00 | −10.00 | −0.810 | | |
| 70%–90% Grey | 7.00 | To Maximum | −10.00 | −0.80 | | |
| Medium to Medium Dark Blonde | | | | | | |
| 40%–60% Grey | 1.70 | 4.00 | 0.00 | 0.00 | | |
| 70%–90% Grey | 4.00 | To Maximum | 0.00 | 0.00 | | |
| Light Blonde Hair | | | | | | |
| 40%–60% Grey | −99.99 | −0.25 | −1.75 | −1.25 | | |
| 70%–90% Grey | −99.99 | −0.25 | −99.99 | −1.75 | | |

*Wherein negative values denote values less than zero.

174. The apparatus according to claim 173, wherein the means for compiling comprises means for assembling the group of lightness measure color factor value ranges in machine-readable, tangible form, and the means for associating comprises means for associating said at least one further color factor value with each lightness measure color factor value range in said machine-readable, tangible form.

* * * * *

UNITED STATES PATENT AND TRADEMARK OFFICE
CERTIFICATE OF CORRECTION

PATENT NO. : 6,128,516
DATED : October 3, 2000
INVENTOR(S) : Macfarlane et al.

It is certified that error appears in the above-identified patent and that said Letters Patent is hereby corrected as shown below:

Title page,
Item [56] References Cited, OTHER PUBLICATIONS:
Under F. Billmeyer, Jr., "Apperance" should read -- Appearance --
Item [57] ABSTRACT, line 3, "ageing" should read -- aging --

Column 12,
Line 22, "subject'coloration," should read -- subject's coloration, --
Line 27, "an" should read -- a --

Column 13,
Line 29, "6," should read -- 6 or --

Column 14,
Line 33, "4," should read -- 4 --

Column 15,
Line 1, "4," should read -- 4 --
Line 6, "4," should read -- 4 --
Line 14, "4," should read -- 4 --

Column 17,
Line 50, "43," should read -- 43 --

Column 18,
Line 49, "51," should read -- 57, --

Column 20,
Line 36, "he" should read -- the --

Column 22,
Line 19, "include" should read -- includes --

Column 24,
Line 9, "accordig" should read -- according --
Line 44, "factors" should read -- factor --

UNITED STATES PATENT AND TRADEMARK OFFICE
CERTIFICATE OF CORRECTION

PATENT NO. : 6,128,516
DATED : October 3, 2000
INVENTOR(S) : Macfarlane et al.

It is certified that error appears in the above-identified patent and that said Letters Patent is hereby corrected as shown below:

Column 25,
Line 26, "subject;" should read -- subject, --
Line 27, "the steps of" should be deleted
Line 50, "coloration;" should read -- coloration, --

Column 26,
Line 7, "coloration;" should read -- coloration, --
Line 50, "coloration;" should read -- coloration, --

Column 30,
Line 38, "coloration;" should read -- coloration, --

Column 33,
Table, col. Hunter L, rows 9–16: "27 to   30" (eight occurrences) should read -- 27 to <30 --

Column 36,
Table, col. Hunter L, rows 9–16: "27 to   30" (eight occurrences) should read -- 27 to <30 --

Column 39,
Line 14, "$\leqq 69$," should read -- $\geq 69$, --

Column 41,
Table, col. a, row Light Red or Red Blonde 40%–60% Grey: " 0. 810" should read -- 0.80 --

Column 1,
Line 34, "IS" should read -- is --

Column 7,
Line 44, "coorelate" should read -- correlate --

Column 8,
Line 51, "inventor'" should read -- inventors' --

UNITED STATES PATENT AND TRADEMARK OFFICE
CERTIFICATE OF CORRECTION

PATENT NO. : 6,128,516
DATED : October 3, 2000
INVENTOR(S) : Macfarlane et al.

It is certified that error appears in the above-identified patent and that said Letters Patent is hereby corrected as shown below:

Column 12,
Line 2, "applicaition" should read -- application --
Line 11, "ben" should read -- been --

Signed and Sealed this

Twenty-sixth Day of March, 2002

Attest:

Attesting Officer

JAMES E. ROGAN
Director of the United States Patent and Trademark Office